United States Patent
Huang et al.

(10) Patent No.: US 12,428,660 B2
(45) Date of Patent: *Sep. 30, 2025

(54) METHODS FOR INCREASING MANNOSE CONTENT OF RECOMBINANT PROTEINS

(71) Applicant: Amgen Inc., Thousand Oaks, CA (US)

(72) Inventors: Chung-Jr Huang, Newbury Park, CA (US); Xiaoming Yang, Oak Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/589,147

(22) Filed: Feb. 27, 2024

(65) Prior Publication Data

US 2024/0200115 A1 Jun. 20, 2024

Related U.S. Application Data

(60) Continuation of application No. 18/134,291, filed on Apr. 13, 2023, now Pat. No. 11,946,085, which is a continuation of application No. 17/867,602, filed on Jul. 18, 2022, now abandoned, which is a continuation of application No. 17/533,004, filed on Nov. 22, 2021, now Pat. No. 11,434,514, which is a continuation of application No. 17/121,419, filed on Dec. 14, 2020, now Pat. No. 11,597,959, which is a continuation of application No. 16/537,490, filed on Aug. 9, 2019, now Pat. No. 10,894,972, which is a continuation of application No. 16/039,123, filed on Jul. 18, 2018, now Pat. No. 10,421,987, which is a continuation of application No. 15/285,392, filed on Oct. 4, 2016, now Pat. No. 10,184,143, which is a division of application No. 14/289,943, filed on May 29, 2014, now Pat. No. 9,481,901.

(60) Provisional application No. 61/828,969, filed on May 30, 2013.

(51) Int. Cl.
C12P 21/00 (2006.01)
C07K 16/00 (2006.01)
C12N 5/00 (2006.01)

(52) U.S. Cl.
CPC ............ C12P 21/005 (2013.01); C07K 16/00 (2013.01); C12N 5/0018 (2013.01); C07K 2317/41 (2013.01); C12N 2500/34 (2013.01)

(58) Field of Classification Search
CPC ... C12P 21/005; C07K 16/00; C07K 2317/41; C12N 5/0018; C12N 2500/34
See application file for complete search history.

(56) References Cited

U.S. PATENT DOCUMENTS

| | | |
|---|---|---|
| 4,695,623 A | 9/1987 | Stabinsky |
| 4,897,471 A | 1/1990 | Stabinsky |
| 4,968,607 A | 11/1990 | Dower |
| 5,075,222 A | 12/1991 | Hannum |
| 5,149,792 A | 9/1992 | Thomason |
| 5,272,064 A | 12/1993 | Thomason |
| 5,395,760 A | 3/1995 | Smith |
| 5,610,279 A | 3/1997 | Brockhaus |
| 5,767,064 A | 6/1998 | Sims |
| 5,856,296 A | 1/1999 | Mosley |
| 5,981,713 A | 11/1999 | Colotta |
| 6,015,938 A | 1/2000 | Boyle |
| 6,096,728 A | 8/2000 | Collins |
| 6,204,363 B1 | 3/2001 | Zsebo |
| 6,235,883 B1 | 5/2001 | Jakobovits |
| 6,238,891 B1 | 5/2001 | Maiorella |
| 6,271,349 B1 | 8/2001 | Dougall |
| 6,337,072 B1 | 1/2002 | Ford |
| 6,544,424 B1 | 4/2003 | Shevitz |
| 6,673,575 B1 | 1/2004 | Franze |
| 7,364,736 B2 | 4/2008 | Boyle |
| 7,645,609 B2 | 1/2010 | Follstad |
| 2016/0002592 A1 | 1/2016 | Shimoni |

FOREIGN PATENT DOCUMENTS

| | | |
|---|---|---|
| AU | 588819 B2 | 9/1989 |
| EP | 0367566 B1 | 5/1997 |
| EP | 0460846 B1 | 2/2002 |
| IN | 2658CHE2009 A | 5/2011 |
| WO | 19940010308 W | 5/1994 |
| WO | 19940028391 W | 12/1994 |
| WO | 19970001633 W | 1/1997 |
| WO | 20010036637 W | 5/2001 |
| WO | 2004008100 A2 | 1/2004 |
| WO | 20120145682 W | 10/2012 |
| WO | 20130006479 W | 1/2013 |
| WO | 2013181575 A2 | 12/2013 |

OTHER PUBLICATIONS

Ahn, et al., Effect of Culture Temperature on Erythropoietin Production and Glycosylation in a Perfusion Culture of Recombinant CHO Cells, Biotechnol Bioeng 101:1234-1244 (2008).
Altamirano, et al., Improvement of CHO Cell Culture Medium Formulation: Simultaneous Substitution of Glucose and Glutamine, Biotechnol Prog, 16:69-75 (2000).
Alton et al., Direct Utilization of Mannose for Mammalian Glycoprotein Biosynthesis, Glycobiology 8:285-295 (1998).
Becker et al., Fucose: Biosynthesis and Biological Function in Mammals, Glycobiology 13:41R-53R (2003).
Berrios, J. et al., Continuous CHO Cell Cultures with Improved Recombinant Protein Productivity by Using Mannose as Carbon Source: Metabolic Analysis and Scale-Up Simulation, Chem. Eng'g Sci. 66:2431-39 (2011).
Brasel et al., Hematologic Effects of flt3 Ligand In Vivo in Mice, Blood 88:2004-2012 (1996).
Cox, R. et al., Studies on the Effects of Simple Sugars on Mammalian Cells in Culture and Characterization of the Inhibition of 3 T3 Fibroblasts by I-Fucose, Cancer Rsch. 28: 1162-72 (1968).

(Continued)

Primary Examiner — Paul J Holland
(74) Attorney, Agent, or Firm — Cynthia T. Chen

(57) ABSTRACT

The present invention relates to methods of upregulating the high mannose glycoform content of a recombinant protein during a mammalian cell culture by manipulating the mannose to total hexose ratio in the cell culture media formulation.

29 Claims, 23 Drawing Sheets

(56) References Cited

OTHER PUBLICATIONS

Do et al., Mechanism of BLyS Action in B Cell Immunity, Cytokine Growth Factor Rev. 13(1):19-25 (2002).

Falck, et al., Glycoform-resolved pharmacokinetic studies in a rat model employing glycoengineered variants of a therapeutic monoclonal antibody, mAbs, 13:1, DOI: 10.1080/19420862.2020.1865596 (2021).

Gao et al., Mannose-6-Phosphate Regulates Destruction of Lipid-Linked Oligosaccharides Mol Biol Cell 22:2994-3009 (2011).

Goetze, et al., High-Mannose Glycans on the Fc Region of Therapeutic IgG Antibodies Increase Serum Clearance in Humans, Glycobiology 21(7):949-959 (2011).

Håkansson et al., Crystal Structure of the Trimeric α-Helical Coiled-Coil and the Three Lectin Domains of Human Lung Surfactant Protein D, Structure 7:255-264 (1999).

Harbury et al., A Switch Between Two-, Three-, and Four-Stranded Coiled Coils in GCN4 Leucine Zipper Mutants, Science 262:1401-1405 (1993).

Harbury et al., Crystal Structure of an Isoleucine-Zipper Trimer, Nature 371:80-83 (1994).

Hills, A. E. et al., Metabolic Control of Recombinant Monocolonal Antibody N-Glycosylation in GS-NSO Cells, Biotechnology & Bioengineering 75(2):239-251 (2001).

Hubbard et al., Synthesis and Processing of Asparagine-Linked Oligosaccharides, Ann. Rev. Biochem., 50:555-583 (1981).

Jayme, D. W., Nutrient Optimization for High Density Biological Production Applications Cytotechnology 5:15-30 (1991).

Kanda, et al., Comparison of biological activity among nonfucosylated therapeutic IgG1 antibodies with three different N-linked Fc oligosaccharides: the high-mannose, hybrid, and complex types, Glycobiology vol. 17 No. 1 pp. 104-118, 2006 doi: 10.1093/glycob/cwl057, Advance Access publication on Sep. 29, 2006.

Kaufman et al., Synthesis, Processing, and Secretion of Recombinant Human Factor VIII Expressed in Mammalian Cells, J Biol Chem, 263:6352-6362 (1988).

Kaufman R.J., Selection and Coamplification of Heterologous Genes in Mammalian Cells, Meth Enzymol, 185:537-566 (1990).

Lovejoy et al., Crystal Structure of a Synthetic Triple-Stranded α-Helical Bundle, Science 259:1288-1293 (1993).

Maisonpierre et al., Angiopoietin-2, a Natural Antagonist for Tie2 That Disrupts In Vivo Angiogenesis, Science 277:55-60 (1997).

Mckinnon et al., Expression, purification and characterization of secreted recombinant human insulin-like growth factor-I (IGF-I) and the potent variant des(1-3)IGF-I in Chinese hamster ovary cells, J Mol Endocrinol 6:231-239 (1991).

NCBI accession No. NM_006682.

Pacis, E. et al., Effects of Cell Culture Conditions on Antibody N-linked Glycosylation—What Affects High Mannose 5 Glycoform, Biotechnology & Bioengineering 108(10):2348-58 (2011).

Panneerselvam et al., Mannose Enters Mammalian Cells Using a Specific Transporter That Is Insensitive to Glucose, J. Bio. Chem. 271(16):9417-21 (1996).

Redacted Complaint & Demand for a Jury Trial for C.A. No. 1:23-cv-2406-CPO-EAP filed May 1, 2023.

Redacted Exhibit A—Factual and Legal Bases for Non-Infringement and Invalidity of Identified Patents for C.A. No. 1:23-cv-2406-CPO-EAP filed Jun. 16, 2023.

Redacted First Amended & Supplemental Complaint & Demand for a Jury Trial for C.A. No. 1:23-cv-2406-CPO-EAP filed Jun. 16, 2023.

Redacted Sandoz Inc.'s Answer, Affirmative Defenses, and Counterclaims To First Amended and Supplemental Complaint for C.A. No. 1:23-cv-2406-CPO-EAP filed Aug. 25, 2023.

Reily et al., "Glycosylation in health and disease", Nature Reviews Nephrology, vol. 15, Issue 6, Mar. 11, 2019.

Rüegg et al., Sequence of a human transcript expressed in T-lymphocytes and encoding a fibrinogen-like protein. Gene 160:257-62 (1995).

Shimadzu, N-Linked Glycan Analysis of Monoclonal Antibodies, Biosimilars, and Glycoproteins with High Resolution Mass Spectrometry and Fluorescence Detection using Restek's Raptor Polar X Column and Protein Metrics' Software Suite, Shimadzu Scientific Instruments, 2020. https://www.ssi.shimadzu.com/sites/ssi.shimadzu.com/files/pim/pim_document_file/ssi/others/14322/Shimadzu_LCMS-116_GlycanAnalysis-LCMS9030.pdf.

Stettler, et al., New Disposable Tubes for Rapid and Precise Biomass Assessment for Suspension Cultures of Mammalian Cells, Biotechnol Bioeng. Dec. 20:95(6):1228-1233 (2006).

Urlaub et al. Isolation of Chinese Hamster Cell Mutants Deficient in Dihydrofolate Reductase Activity, Proc Natl Acad Sci USA, 77:4216-4220 (1980).

Vattepu, et al., "Sialylation as an Important Regulator of Antibody Function", Frontiers in Immunology, vol. 13, Apr. 7, 2022.

Voisard et al., Potential of Cell Retention Techniques for Large-Scale High-Density Perfusion Culture of Suspended Mammalian Cells, Biotechnology and Bioengineering 82:751-65 (2003).

Wong et al. Impact of Dynamic Online Fed-Batch Strategies on Metabolism, Productivity and N-Glycosylation Quality in CHO Cell Cultures, Biotechnol Bioeng 89:164-177 (2005).

Wood et al., High level synthesis of immunoglobulins in Chinese hamster ovary cells. J. Immunol. 145:3011-3016 (1990).

Yu, et al., Production, Characterization and Pharmacokinetic Properties of Antibodies withGlycans, MAbs 4:475-487 (2012).

METHODS FOR INCREASING MANNOSE CONTENT OF RECOMBINANT PROTEINS

CROSS REFERENCE TO RELATED APPLICATIONS

This application is a continuation of U.S. patent application Ser. No. 18/134,291, filed Apr. 13, 2023, which is a continuation of U.S. patent application Ser. No. 17/867,602, filed Jul. 18, 2022, which is a continuation of U.S. patent application Ser. No. 17/533,004, filed Nov. 22, 2021, now U.S. Pat. No. 11,434,514, which is a continuation of U.S. patent application Ser. No. 17/121,419, filed Dec. 14, 2020, now U.S. Pat. No. 11,597,959, which is a continuation of U.S. patent application Ser. No. 16/537,490, filed Aug. 9, 2019, now U.S. Pat. No. 10,894,972, which is a continuation of U.S. patent application Ser. No. 16/039,123, filed Jul. 18, 2018, now U.S. Pat. No. 10,421,987, which is a continuation of U.S. patent application Ser. No. 15/285,392, filed Oct. 4, 2016, now U.S. Pat. No. 10,184,143, which is a divisional of U.S. patent application Ser. No. 14/289,943, filed May 29, 2014, now U.S. Pat. No. 9,481,901, which claims the benefit of U.S. Provisional Application 61/828,969, filed May 30, 2013, the content of which is incorporated herein by reference in its entirety.

BACKGROUND OF INVENTION

Glycoforms of a protein expressed by Chinese hamster ovary (CHO) host cell are largely determined during cell line generation and clone selection. However, high mannose glycoform content can also be affected by cell culture conditions (Pacis et al., (2011) *Biotechnol Bioeng* 108, 2348-2358). Proteins produced in mammalian cell cultures may contain varied levels of high mannose glycoforms such as Mannose5 (Man5), Mannose6 (Man6), Mannose7 (Man7), Mannose8 (Man8) and Mannose9 (Man9). High mannose glycoform content of therapeutic proteins is a critical quality attribute that has been found to affect pharmacokinetic properties of certain therapeutic antibodies (Goetze, et al., (2011) Glycobiology 21, 949-59; Yu, et al., 2012) *MAbs* 4, 475-87).

It is common in therapeutic protein industry to seek a desired range of high mannose glycoform content for a protein product due to process changes, scale-up, improvements or the need to match existing antibody quality attributes. Methods for manipulating high mannose glycoform content of a protein in cell culture include changes in media compositions, osmolality, pH, temperature, etc (Yu, et al., supra, Pacis et al., supra, Chee Furng Wong et al., (2005) *Biotechnol Bioeng* 89, 164-177; Ahn, et al., (2008) *Biotechnol Bioeng* 101, 1234-44). Lower temperatures, such as below 32° C., have been shown to increase high mannose glycoforms and reduce antennary structure and sialylation of recombinant erythropoietin (Ahn et al. (2008) Biotechnol Bioeng 101, 1234-44). Recently, Pacis and colleagues demonstrated that antibody Man5 level can be increased more than two-fold from 12% to 28% by increasing medium osmolarity and culture duration time (Pacis et al., supra). The effectiveness of these methods is specific to cell lines, molecule types and media environment and is typically obtained by trial and error. Additionally, these methods tend to also alter antibody productivity, cell culture behavior and other antibody quality attributes.

Therefore there is a need for a method for predictably manipulating high mannose glycoform regulation. Such a method would benefit the process development of therapeutic proteins. The invention provides a method that regulates high mannose glycoform content by manipulating the mannose to total hexose ratio in cell culture media.

SUMMARY OF THE INVENTION

The present invention provides a cell culture media containing mannose, wherein the mannose to total hexose ratio in the cell culture media is greater than 0 but less than 1.0. In one embodiment the mannose to total hexose ratio in the cell culture media is greater than or equal to 0.25. In one embodiment the mannose to total hexose ratio in the cell culture media is greater than or equal to 0.5. In another embodiment the mannose to total hexose ratio in the cell culture media is greater than or equal to 0.75. In another embodiment the mannose to total hexose ratio in the cell culture media is less than or equal to 0.94. In another embodiment the cell culture media contains at least 3 g/L mannose. In another embodiment the cell culture media contains at least 6 g/L mannose. In another related embodiment the cell culture media contains at least 9 g/L mannose. In another embodiment the cell culture media contains at least 11.25 g/L mannose. In another embodiment is provided use of a cell culture media described above for upregulating the high mannose glycoform content of a recombinant protein during a mammalian cell culture process.

The present invention provides a method for upregulating the high mannose glycoform content of a recombinant protein during a mammalian cell culture process comprising; establishing a mammalian cell culture in a bioreactor with a cell culture media that does not contain mannose; and maintaining the cell culture with a cell culture media containing mannose, wherein the mannose to total hexose ratio in the cell culture media is greater than 0 but less than 1.0. In one embodiment the cell culture is maintained by perfusion. In one embodiment perfusion begins on or about day 3 to on or about day 9 of the cell culture. In a related embodiment perfusion begins on or about day 3 to on or about day 7 of the cell culture. In one embodiment perfusion begins when the cells have reached a production phase. In one embodiment perfusion comprises continuous perfusion. In one embodiment the rate of perfusion is constant. In one embodiment perfusion is performed at a rate of less than or equal to 1.0 working volumes per day. In one embodiment the cell culture receives bolus cell culture media feeds prior to days 3-7 of the culture. In one embodiment the mammalian cell culture is established by inoculating the bioreactor with at least $0.5 \times 10^6$ to $3.0 \times 10^6$ cells/mL in a serum-free culture media. In one embodiment the mammalian cell culture is established by inoculating the bioreactor with at least $0.5 \times 10^6$ to $1.5 \times 10^6$ cells/mL in a serum-free culture media. In one embodiment the invention further comprises a temperature shift from 36° C. to 31° C. In one embodiment the invention further comprises a temperature shift is from 36° C. to 33° C. In a related embodiment the temperature shift occurs at the transition between the growth phase and production phase. In a related embodiment the temperature shift occurs during the production phase. In another embodiment the invention further comprises inducing cell growth-arrest by L-asparagine starvation followed by perfusion with a serum-free perfusion media having an L-asparagine concentration of 5 mM or less. In another embodiment the invention further comprises inducing cell growth-arrest by perfusion with a serum-free perfusion media having an L-asparagine concentration of 5 mM or less. In a related embodiment the concentration of L-asparagine in the serum-free perfusion media is less than or equal to 5 mM. In a related embodiment the concentration of L-asparagine in the serum-free perfusion media is less than or equal to 4.0 mM. In a related embodiment the concentration of L-asparagine in the serum-free perfusion media is less than or equal to 3.0 mM. In a related embodiment the concentration of L-asparagine in the serum-free perfusion media is less than or equal to 2.0 mM. In a related embodiment the concentration of L-asparagine in the serum-free perfusion media is less than or equal to 1.0 mM. In a related embodiment the concentration of L-asparagine in the serum-free perfusion media is 0 mM. In a related embodiment the L-asparagine concentration of the cell culture media is monitored prior to and during L-asparagine starvation. In yet another embodiment the invention comprises that the packed cell volume during a production phase is less than or equal to 35%. In a related embodiment the packed cell volume is less than or equal to 35%. In a related embodiment the packed cell volume is less than or equal to 30%. In a related embodiment the viable cell density of the mammalian cell culture at a packed cell volume less than or equal to 35% is $10\times10^6$ viable cells/ml to $80\times10^6$ viable cells/ml. In another embodiment the viable cell density of the mammalian cell culture is $20\times10^6$ viable cells/ml to $30\times10^6$ viable cells/ml. In another embodiment the perfusion is accomplished by alternating tangential flow. In a related embodiment the perfusion is accomplished by alternating tangential flow using an ultrafilter or a microfilter. In yet another embodiment the bioreactor has a capacity of at least 500 L. In yet another embodiment the bioreactor has a capacity of at least 500 L to 2000 L. In yet another embodiment the bioreactor has a capacity of at least 1000 L to 2000 L. In yet another embodiment the mammalian cells are Chinese Hamster Ovary (CHO) cells. In yet another embodiment the recombinant protein is selected from the group consisting of a human antibody, a humanized antibody, a chimeric antibody, a recombinant fusion protein, or a cytokine. In yet another embodiment the invention further comprises a step of harvesting the recombinant protein produced by the cell culture. In a further embodiment the recombinant protein produced by the cell culture is purified and formulated in a pharmaceutically acceptable formulation. In a further embodiment the high mannose glycoform content of a recombinant protein is increased compared to a culture where the cells are not subjected to a cell culture media containing a mannose to total hexose ratio of greater than 0 and less than 1.0.

The present invention provides a method for upregulating the high mannose glycoform content of a recombinant protein during a mammalian cell culture process comprising: establishing a mammalian cell culture in a bioreactor with a cell culture media that does not contain mannose; growing the mammalian cells during a growth phase with a cell culture media that does not contain mannose; initiating and maintaining a production phase in the cell culture by perfusion with a serum-free perfusion media containing mannose, wherein the mannose to total hexose ratio in the perfusion media is greater than 0 but less than 1.0.

DETAILED DESCRIPTION OF THE INVENTION

Figure 1A:
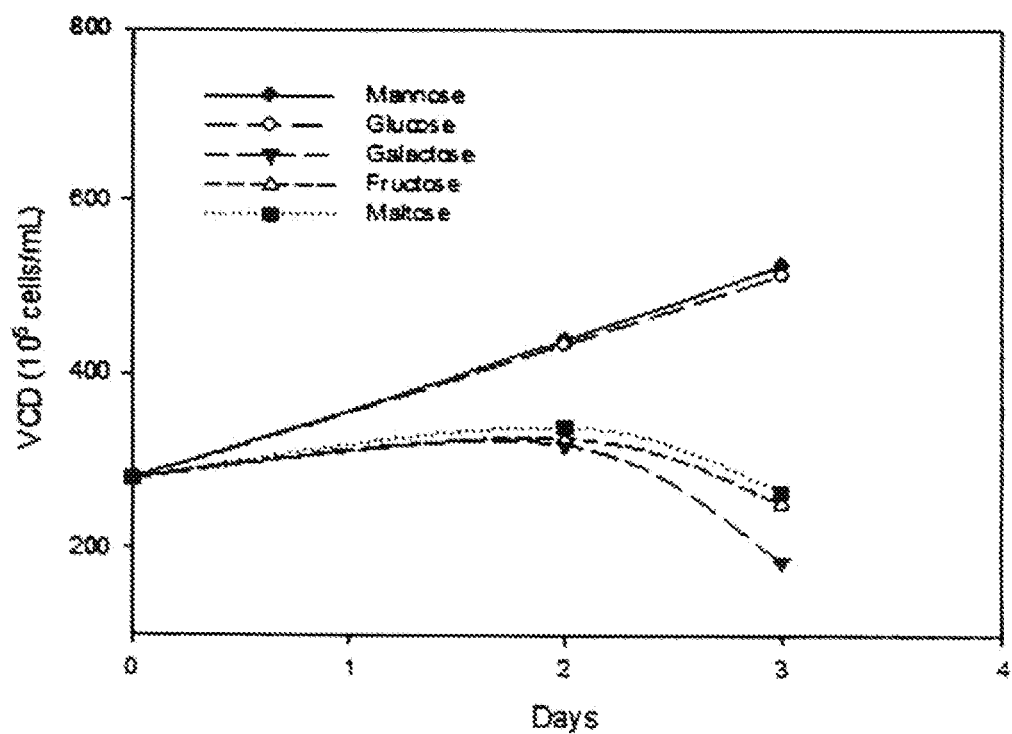
FIG. 1A shows a graph of effects of different carbon sources on viable cell density.

High-mannose glycoforms (HM) are increasingly recognized as critical quality attributes for therapeutic protein products. Previous attempts to control high mannose glycoform content have been essentially empirical and it has been challenging to target desired high-mannose content during recombinant protein process development. As described herein, the high mannose glycoform content on recombinant proteins may be controlled by manipulating the ratio of mannose to total hexose in the cell culture media. Such manipulation was found to be predictive, scalable, linear and applicable to different cell lines, making this method a powerful tool for upregulating the percent of high mannose glycoforms in a more predictable manner. The inventive method precisely controls the percent of high mannose glycoforms of a recombinant protein without compromising cell growth and titer.

The present invention provides a cell culture media containing mannose, wherein the mannose to total hexose ratio in the cell culture media is greater than 0 but less than 1.0 and use of such cell culture media for upregulating the high mannose glycoform content of a recombinant protein during a mammalian cell culture process. As demonstrated herein, advantage may be taken of the correlation between high mannose glycoform content on recombinant proteins and the mannose to total hexose ratio in the cell culture media. Modulating glycoform content in such a manner is a powerful tool to manipulate a critical attribute of a therapeutic protein.

The invention provides a method for upregulating high mannose glycoforms to achieve desired product quality attributes while maintaining desirable levels of certain cell culture parameters such as volumetric productivity, cell viability, and/or density. The method makes us of a cell culture media wherein the mannose to total hexose ratio is between 0 and 1.10. Also provided is a method for upregulating the high mannose glycoform content of a recombinant protein during a mammalian cell culture process comprising; establishing a mammalian cell culture in a bioreactor with a cell culture media that does not contain mannose; and maintaining the cell culture with a cell culture media containing mannose, wherein the mannose to total hexose ratio in the cell culture media is greater than 0 but less than 1.0.

As used herein, high mannose glycoforms (HM, usually provided as a percentage) refers to a protein having one or more high mannose glucans attached. High mannose glycans include Mannose-5, Mannose-6, Mannose-7, Mannose-8 and Mannose-9.

Mannose to total hexose ratio (M/H) is determined by dividing the amount of hexose (including mannose) by the amount of mannose in the liquid media that is fed into the bioreactor. For example, if the media contains 6 g/L mannose and 6 g/L glucose, the M/H ratio is 0.5. Hexose refers to a monosaccharide having 6 carbon atoms per molecule, such as mannose, glucose, galactose and fructose.

Carbohydrate moieties are described herein with reference to commonly used nomenclature for oligosaccharides. A review of carbohydrate chemistry which uses this nomenclature can be found, for example, in Hubbard and Ivatt, Ann. Rev. Biochem. 50:555-583 (1981).

For the purposes of this invention, cell culture medium is a medium suitable for growth of animal cells, such as mammalian cells, in in vitro cell culture. Cell culture media formulations are well known in the art. Typically, cell culture media are comprised of buffers, salts, carbohydrates, amino acids, vitamins and trace essential elements. Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kansas), among others. Serum-free versions of such culture media are also available. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

Cell culture media may be serum-free, protein-free, and/or peptone-free. "Serum-free" applies to a cell culture medium that does not contain animal sera, such as fetal bovine serum. "Protein-free" applies to cell culture media free from exogenously added protein, such as transferrin, protein growth factors IGF-1, or insulin. Protein-free media may or may not contain peptones. "Peptone-free" applies to cell culture media which contains no exogenous protein hydrolysates such as animal and/or plant protein hydrolysates. Cell culture broth, or like terminology, refers to the cell culture media that contains, among other things, viable and non-viable mammalian cells, cell metabolites and cellular debris such as nucleic acids, proteins and liposomes.

For upregulating the high mannose glycoform content of a recombinant antibody, the cell culture media of the present invention contains mannose, wherein the mannose to total hexose ratio in the cell culture media is greater than 0 but less than 1.0. The ratio may be 0.1, 0.2, 0.3, 0.5, 0.6, 0.7, 0.8, 0.9, 0.10, 0.15, 0.20, 0.25, 0.30, 0.35, 0.40, 0.45, 0.50, 0.55, 0.60, 0.65, 0.70, 0.75, 0.80, 0.5, 0.90, 0.91, 0.92, 0.93, 0.94, 0.95, 0.96, 0.97, 0.98 or 0.99 or any value in between. The concentration of mannose in the cell culture media is preferably at least 3 g/l, at least 6 g/L, at least 9 g/L, or at least 11 g/L. Preferably the concentration of mannose is greater than 11 g/L. Preferably the concentration of mannose is 11.01, 11.05, 11.10, 11.15, 11.20, 11.25, 11.30, 11.35, 11.40, 11.45, 11.50, 11.55, 11.60, 11.65, 11.70, 11.75, 11.80, 11.85, 11.90, 11.95 g/L or any value in between. In a preferred embodiment, the amount of mannose is 11.35 g/L. Preferably the cell culture media also contains glucose at such a concentration that the mannose to hexose ratio is greater than 0 but less than 1.0. In one embodiment the amount of glucose is at least 0.75 g/L to 12 g/L. In a preferred embodiment the amount of glucose is 0.75 g/L.

Cell cultures can also be supplemented with concentrated feed medium containing components, such as nutrients and amino acids, which are consumed during the course of the production phase of the cell culture, see for example WIPO Publication No WO2012/145682. Concentrated feed medium may be based on just about any cell culture media formulation. Such a concentrated feed medium can contain anywhere from a single or nearly almost all of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal amount.

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate. Fluidized bed bioreactors, hollow fiber bioreactors, roller bottles, shake flasks, or stirred tank bioreactors, with or without microcarriers, can be used.

The mammalian cell culture is grown in a bioreactor. In one embodiment 500 L to 20000 L bioreactors are used. In a preferred embodiment, 1000 L to 2000 L bioreactors are used.

The bioreactor may be inoculated with at least $0.5 \times 10^6$ and up to and beyond $3.0 \times 10^6$ viable cells/mL in a serum-free culture medium. In a preferred embodiment the inoculation is $1.0 \times 10^6$ viable cells/mL.

Once inoculated into the production bioreactor the mammalian cells undergo an exponential growth phase. The growth phase can be maintained as a batch culture, using a fed-batch process with bolus feeds of a feed medium, as a perfusion culture, or any combination. For fed batch methods, supplemental bolus feeds typically begin shortly after the cells are inoculated into the bioreactor, at a time when it is anticipated, estimated or determined that the cell culture needs feeding. For example, supplemental feeds can begin on or about day 3 or 4 of the culture or a day or two earlier or later. The culture may receive two, three, or more bolus feeds during the growth phase. For cultures maintained by perfusion, perfusion feeds can begin at any time, for example, perfusion feeds can begin on or about day 3 or 4 of the culture or a day or two earlier or later.

When the cells enter the stationary or production phase, or the cell culture has achieved a desired viable cell density and/or cell titer, the fed batch bolus feeds can be discontinued and perfusion feeds started. Perfusion culture is one in which the cell culture receives fresh perfusion feed medium while simultaneously removing spent medium. Perfusion can be continuous, step-wise, intermittent, or a combination of any or all of any of these. Perfusion rates can be less than a working volume to many working volumes per day. Preferably the cells are retained in the culture and the spent medium that is removed is substantially free of cells or has significantly fewer cells than the culture. Perfusion can be accomplished by a number of means including centrifugation, sedimentation, or filtration, See e.g. Voisard et al., (2003), Biotechnology and Bioengineering 82:751-65. A preferred filtration method is alternating tangential flow filtration. Alternating tangential flow is maintained by pumping medium through hollow-fiber filter modules. See e.g. U.S. Pat. No. 6,544,424. The hollow-fiber modules can be microfilters or ultrafilters.

When the fed-batch culture reaches a predetermined trigger point, such as desired cell viability, cell density, percent packed cell volume, titer, packed cell volume adjusted titer, age or the like, a switch between fed-batch and perfusion can take place. For example, this switch can take place on or about day 7 of the culture, but may take place a day or two earlier or later. The perfusion feed formulation may contain glucose at a concentration of up to 14 g/L or more. In one embodiment, the perfusion medium contains 12 g/L glucose.

Upregulation of glycoform content can begin at any stage at or after the cells are inoculated into the production bioreactor, during the growth phase, at the start of the production phase, during the production phase. Bolus feeds and/or perfusion media may contain concentrations of mannose such as to give a mannose to total hexose ratio of greater than 0 but less than 1.0.

When the perfusion culture reaches a predetermined trigger point, such as desired cell viability, cell density, percent packed cell volume, titer, packed cell volume adjusted titer, age or the like, mannose may be added to the media such as to give a mannose to total hexose ratio of greater than 0 but less than 1.0. For example, this shift may be initiated on day 11 of the culture, but may take place a day or two earlier or later. At that time the cell culture is perfused with cell culture medium containing mannose such that the mannose to total hexose ratio is greater than 0 but less than 1.0. The ratio may be 0.1, 0.2, 0.3, 0.5, 0.6, 0.7, 0.8, 0.9, 0.10, 0.15, 0.20, 0.25, 0.30, 0.35, 0.40, 0.45, 0.50, 0.55, 0.60, 0.65, 0.70, 0.75, 0.80, 0.5, 0.90, 0.91, 0.92, 0.93, 0.94, 0.95, 0.96, 0.97, 0.98 or 0.99 or any value in between. The concentration of mannose in the cell culture media is preferably at least 3 g/l, at least 6 g/L, at least 9 g/L, or at least 11 g/L. Preferably the concentration of mannose is greater than 11 g/L. Preferably the concentration of mannose is 11.01, 11.05, 11.10, 11.15, 11.20, 11.25, 11.30, 11.35, 11.40, 11.45, 11.50, 11.55, 11.60, 11.65, 11.70, 11.75, 11.80, 11.85, 11.90, 11.95 g/L or any value in between. In a preferred embodiment, the amount of mannose is 11.35 g/L. Preferably the cell culture media also contains glucose at such a concentration that the mannose to hexose ratio is greater than 0 but less than 1.0. In another embodiment the amount of glucose is at least 0.75 g/L to 12 g/L. In one embodiment, the amount of glucose is 0.75 g/L.

The mannose to total hexose ratio in the cell culture is determined and maintained by monitoring the concentration of mannose and hexose sugars in the cell culture media added to the bioreactor, and adjusting the mannose and hexose sugar concentration in the medium formulation to maintain a ratio of greater than 0 but less than 1.0. Samples may also be taken from the bioreactor or the spent media to determine the mannose to total hexose ratio.

The cell culture can be continuously maintained or harvested. The cell culture can be restored to a state where the mannose to total hexose ratio is greater than 1.0 via supplements to the cell culture media or a reformulation of the feed media and the entire process begun again as is desired.

The cell culture could also be maintained in a perfusion culture system for both the growth and production phases. Once inoculated into the production bioreactor the mammalian cells undergo an exponential growth phase. If desired, the cell culture may be supplemented with mannose such as to maintain a mannose to total hexose ratio of greater than 0 but less than 1.0. The culture is maintained until a desired trigger point is achieved, for example, desired viable cell density, cell viability, percent packed cell volume, titer, packed cell adjusted volume titer, age or the like, that signals the start of a production phase. At that time or at any time during the production phase, the cell culture may be perfused with a cell culture medium supplemented with mannose such that the mannose to total hexose ratio is greater than 0 but less than 1.0. The ratio may be 0.1, 0.2, 0.3, 0.5, 0.6, 0.7, 0.8, 0.9, 0.10, 0.15, 0.20, 0.25, 0.30, 0.35, 0.40, 0.45, 0.50, 0.55, 0.60, 0.65, 0.70, 0.75, 0.80, 0.5, 0.90, 0.91, 0.92, 0.93, 0.94, 0.95, 0.96, 0.97, 0.98 or 0.99 or any value in between. The concentration of mannose in the cell culture media is preferably at least 3 g/l, at least 6 g/L, at least 9 g/L, or at least 11 g/L or more. Preferably the concentration of mannose is greater than 11 g/L. Preferably the concentration of mannose is 11.01, 11.05, 11.10, 11.15, 11.20, 11.25, 11.30, 11.35, 11.40, 11.45, 11.50, 11.55, 11.60, 11.65, 11.70, 11.75, 11.80, 11.85, 11.90, 11.95 g/L or any value in between. In a preferred embodiment, the amount of mannose is 11.35 g/L. Preferably the cell culture media also contains glucose at such a concentration that the mannose to hexose ratio is greater than 0 but less than 1.0. In another embodiment the amount of glucose is at least 0.75 g/L to 12 g/L. In one embodiment, the amount of glucose is 0.75 g/L.

Viable cell density may be a signal for transition to the production phase or trigger use of a cell culture media having a mannose to total hexose ratio of greater than 0 but less than 1.0 to the cell culture media. It may also be desirable to maintain a certain range or level of viable cell density during the production phase or while using a cell culture media having a mannose to total hexose ratio is greater than 0 bur less than 1.0. In one embodiment the viable cell density is $10 \times 10^6$ viable cells/mL to at least about $60 \times 10^6$ viable cells/mL. In another embodiment the viable cell density is $10 \times 10^6$ viable cells/mL to $50 \times 10^6$ viable cells/mL. In another embodiment the viable cell density is $10 \times 10^6$ viable cells/mL to $40 \times 10^6$ viable cells/mL. In a preferred embodiment the viable cell density is $10 \times 10^6$ viable cells/mL to $30 \times 10^6$ viable cells/mL. In another preferred embodiment the viable cell density is $10 \times 10^6$ viable cells/mL to $20 \times 10^6$ viable cells/mL. In another preferred embodiment the viable cell density is $20 \times 10^6$ viable cells/mL to $30 \times 10^6$ viable cells/mL. In yet another preferred embodiment the viable cell density is $20 \times 10^6$ viable cells/mL to $25 \times 10^6$ viable cells/mL. In an even more preferred embodiment the viable cell density is at least about $20 \times 10^6$ viable cells/mL.

The percent packed cell volume (% PCV) may also be used as a signal for transition to the production phase or trigger use of a cell culture media having a mannose to total hexose ratio of greater than 0 but less than 1.0 to the cell culture media. The cell culture may also be maintained at a desired packed cell volume during the production phase or while using a cell culture media having a mannose to total hexose ratio of 0 to 1.0. In one embodiment the packed cell volume is equal to or less than 30%. In a preferred embodiment the packed cell volume is at least about 15-30%. In a preferred embodiment the packed cell volume is at least about 20-25%. In another preferred embodiment the packed cell volume is equal to or less than 25%. In another preferred embodiment the packed cell volume is equal to or less than 15%. In another preferred embodiment the packed cell volume is equal to or less than 20%. In yet another preferred embodiment the packed cell volume is equal to or less than 15%.

A perfusion cell culture medium having a reduced concentration of asparagine can be used to arrest cell growth while maintaining productivity and viability during the production phase or in a cell culture media having a mannose to total hexose ratio of greater than 0 to less than 1.0. In a preferred embodiment the concentration of asparagine is at least about 0 mM to at least about 5 mM asparagine, sec WIPO Publication No. WO 2013/006479.

As used herein, "perfusion flow rate" is the amount of media that is passed through (added and removed) from a bioreactor, typically expressed as some portion or multiple of the working volume, in a given time. "Working volume" refers to the amount of bioreactor volume used for cell culture. In one embodiment the perfusion flow rate is one working volume or less per day. Perfusion feed medium can be formulated to maximize perfusion nutrient concentration to minimize perfusion rate.

As used herein, "cell density" refers to the number of cells in a given volume of culture medium. "Viable cell density" refers to the number of live cells in a given volume of culture medium, as determined by standard viability assays (such as trypan blue dye exclusion method).

As used herein, "packed cell volume" (PCV), also referred to as "percent packed cell volume" (% PCV), is the ratio of the volume occupied by the cells, to the total volume of cell culture, expressed as a percentage (see Stettler, wt al., (2006) Biotechnol Bioeng. Dec 20:95(6):1228-33). Packed cell volume is a function of cell density and cell diameter; increases in packed cell volume could arise from increases in either cell density or cell diameter or both. Packed cell volume is a measure of the solid content in the cell culture. Solids are removed during harvest and downstream purification. More solids mean more effort to separate the solid material from the desired product during harvest and downstream purification steps. Also, the desired product can become trapped in the solids and lost during the harvest process, resulting in a decreased product yield. Since host cells vary in size and cell cultures also contain dead and dying cells and other cellular debris, packed cell volume is a more accurate way to describe the solid content within a cell culture than cell density or viable cell density.

The method according to the present invention may be used to improve the production of recombinant proteins in a multiple phase culture process. In a multiple stage process, cells are cultured in two or more distinct phases. For example cells may be cultured first in one or more growth phases, under environmental conditions that maximize cell proliferation and viability, then transferred to a production phase, under conditions that maximize protein production. In a commercial process for production of a protein by mammalian cells, there are commonly multiple, for example, at least about 2, 3, 4, 5, 6, 7, 8, 9, or 10 or more growth phases that occur in different culture vessels preceding a final production culture. The growth and production phases may be preceded by, or separated by, one or more transition phases. In multiple phase processes, the method according to the present invention can be employed at least during the growth and production phase of the final production phase of a commercial cell culture, although it may also be employed in any of the preceding growth, transition and/or production phases. A production phase can be conducted at large scale. A large scale process can be conducted in a volume of at least about 100, 500, 1000, 2000, 3000, 5000, 7000, 8000, 10,000, 15,000, or 20,000 liters or more. In a preferred embodiment production is conducted in 500 L, 1000 L and/or 2000 L bioreactors. A growth phase may occur at a higher temperature than a production phase. For example, a growth phase may occur at a first temperature from about 35° C. to about 38° C., and a production phase may occur at a second temperature from about 29° C. to about 37° C., optionally from about 30° C. to about 36° C.

or from about 30° C. to about 34° C. In addition, chemical inducers of protein production, such as, for example, caffeine, butyrate, and/or hexamethylene bisacetamide (HMBA), may be added at the same time as, before, and/or after a temperature shift. If inducers are added after a temperature shift, they can be added from one hour to five days after the temperature shift, optionally from one to two days after the temperature shift. The cell cultures can be maintained for days or even weeks while the cells produce the desired protein(s).

Typically the cell cultures that precede the final production culture (N–x to N–1) are used to generate the seed cells that will be used to inoculate the production bioreactor, the N–1 culture. The seed cell density can have a positive impact on the level of recombinant protein produced. Product levels tend to increase with increasing seed density. Improvement in titer is tied not only to higher seed density, but is likely to be influenced by the metabolic and cell cycle state of the cells that are placed into production.

Seed cells can be produced by any culture method. A preferred method is a perfusion culture using alternating tangential flow filtration. An N–1 bioreactor can be run using alternating tangential flow filtration to provide cells at high density to inoculate a production bioreactor. The N–1 stage may be used to grow cells to densities of >90×10$^6$ cells/mL. The N–1 bioreactor can be used to generate bolus seed cultures or can be used as a rolling seed stock culture that could be maintained to seed multiple production bioreactors at high seed cell density. The duration of the growth stage of production can range from 7 to 14 days and can be designed so as to maintain cells in exponential growth prior to inoculation of the production bioreactor. Perfusion rates, medium formulation and timing are optimized to grow cells and deliver them to the production bioreactor in a state that is most conducive to optimizing their production. Seed cell densities of >15×10$^6$ cells/mL can be achieved for seeding production bioreactors.

The cell lines (also referred to as "host cells") used in the invention are genetically engineered to express a polypeptide of commercial or scientific interest. Cell lines are typically derived from a lineage arising from a primary culture that can be maintained in culture for an unlimited time. Genetically engineering the cell line involves transfecting, transforming or transducing the cells with a recombinant polynucleotide molecule, and/or otherwise altering (e.g., by homologous recombination and gene activation or fusion of a recombinant cell with a non-recombinant cell) so as to cause the host cell to express a desired recombinant polypeptide. Methods and vectors for genetically engineering cells and/or cell lines to express a polypeptide of interest are well known to those of skill in the art; for example, various techniques are illustrated in *Current Protocols in Molecular Biology*, Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., *Large Scale Mammalian Cell Culture,* 1990, pp. 15-69.

Animal cell lines are derived from cells whose progenitors were derived from a multicellular animal. One type of animal cell line is a mammalian cell line. A wide variety of mammalian cell lines suitable for growth in culture are available from the American Type Culture Collection (Manassas, Va.) and commercial vendors. Examples of cell lines commonly used in the industry include VERO, BHK, HeLa, CVI (including Cos), MDCK, 293, 3T3, myeloma cell lines (e.g., NSO, NS1), PC12, WI38 cells, and Chinese hamster ovary (CHO) cells. CHO cells are widely used for the production of complex recombinant proteins, e.g. cytokines, clotting factors, and antibodies (Brasel et al. (1996), *Blood* 88:2004-2012; Kaufman et al. (1988), *J Biol Chem* 263: 6352-6362; Mckinnon et al. (1991), *J Mol Endocrinol* 6:231-239; Wood et al. (1990), *J. Immunol.* 145:3011-3016). The dihydrofolate reductase (DHFR)-deficient mutant cell lines (Urlaub et al. (1980), *Proc Natl Acad Sci USA* 77: 4216-4220), DXB11 and DG-44, are desirable CHO host cell lines because the efficient DHFR selectable and amplifiable gene expression system allows high level recombinant protein expression in these cells (Kaufman R. J. (1990), *Meth Enzymol* 185:537-566). In addition, these cells are easy to manipulate as adherent or suspension cultures and exhibit relatively good genetic stability. CHO cells and proteins recombinantly expressed in them have been extensively characterized and have been approved for use in clinical commercial manufacturing by regulatory agencies.

The methods of the invention can be used to culture cells that express recombinant proteins of interest. The expressed recombinant proteins may be secreted into the culture medium from which they can be recovered and/or collected. In addition, the proteins can be purified, or partially purified, from such culture or component (e.g., from culture medium) using known processes and products available from commercial vendors. The purified proteins can then be "formulated", meaning buffer exchanged, sterilized, bulk-packaged, and/or packaged for a final user. Suitable formulations for pharmaceutical compositions include those described in *Remington's Pharmaceutical Sciences,* 18th ed. 1995, Mack Publishing Company, Easton, PA.

As used herein "peptide," "polypeptide" and "protein" are used interchangeably throughout and refer to a molecule comprising two or more amino acid residues joined to each other by peptide bonds. Polypeptides can be of scientific or commercial interest, including protein-based drugs. Polypeptides include, among other things, antibodies, fusion proteins, and cytokines. Peptides, polypeptides and proteins can be produced by recombinant animal cell lines using cell culture methods and may be referred to as "recombinant peptide", "recombinant polypeptide" and "recombinant protein". The expressed protein(s) may be produced intracellularly or secreted into the culture medium from which it can be recovered and/or collected.

Peptides, polypeptides and proteins are also inclusive of modifications including, but not limited to, glycosylation, lipid attachment, sulfation, gamma-carboxylation of glutamic acid residues, hydroxylation and ADP-ribosylation. "Glycoprotein" refers to peptides, polypeptides and proteins, having at least one oligosaccharide side chain including mannose residues. Glycoproteins may be homologous to the host cell, or may be heterologous, i.e., foreign, to the host cell being utilized, such as, for example, a human glycoprotein produced by a Chinese hamster ovary (CHO) host-cell.

Examples of polypeptides that can be produced with the methods of the invention include proteins comprising amino acid sequences identical to or substantially similar to all or part of one of the following proteins: tumor necrosis factor (TNF), flt3 ligand (WO 94/28391), erythropocitin, thrombopocitin, calcitonin, IL-2, angiopoietin-2 (Maisonpierre et al. (1997), *Science* 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM_00682; Rüegg and Pytela (1995), *Gene* 160:257-62) growth hormone, insulin, insulinotropin, insulin-like growth factors, parathyroid hormone, interferons including α-interferons, γ-interferon, and consensus interferons (U.S. Pat. Nos. 4,695,623 and 4,897, 471), nerve growth factor, brain-derived neurotrophic factor, synaptotagmin-like proteins (SLP 1-5), neurotrophin-3, glucagon, interleukins, colony stimulating factors, lymphotoxin-β, leukemia inhibitory factor, and oncostatin-M. Descriptions of other glycoproteins may be found in, for example, *Human Cytokines: Handbook for Basic and Clinical Research*, all volumes (Aggarwal and Gutterman, eds. Blackwell Sciences, Cambridge, MA, 1998); *Growth Factors: A Practical Approach* (McKay and Leigh, eds., Oxford University Press Inc., New York, 1993); and *The Cytokine Handbook*, Vols. 1 and 2 (Thompson and Lotze eds., Academic Press, San Diego, CA, 2003).

Additionally the methods of the invention would be useful to produce proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. Nos. 5,395,760 and 5,610,279), Interleukin-1 (IL-1) receptors (types I and II; EP Patent No. 0460846, U.S. Pat. Nos. 4,968,607, and 5,767,064,), IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other proteins that can be produced using the invention include proteins comprising all or part of the amino acid sequences of differentiation antigens (referred to as CD proteins) or their ligands or proteins substantially similar to either of these. Such antigens are disclosed in *Leukocyte Typing VI* (*Proceedings of the VIth International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be produced by the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

The term "antibody" includes reference to immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof. Also included are proteins having an antigen binding fragment or region such as Fab, Fab', F(ab')$_2$, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792), VEGF, TGF, TGF-β2, TGF-β1, EGF receptor (see U.S. Pat. No. 6,235, 883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), *Cytokine Growth Factor Rev.* 13(1): 19-25), C5 complement, IgE, tumor antigen CA125, tumor antigen MUCI, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphylococcus aureus*. Specific examples of known antibodies which can be produced using the methods of the invention include but are not limited to adalimumab, bevacizumab, infliximab, abciximab, alemtuzumab, bapincuzumab, basiliximab, belimumab, briakinumab, canakinumab, certolizumab pegol, cetuximab, conatumumab, denosumab, eculizumab, gemtuzumab ozogamicin, golimumab, ibritumomab tiuxctan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, vedolizumab, zalutumumab, and zanolimumab.

The invention can be used to produce recombinant fusion proteins comprising, for example, any of the above-mentioned proteins. For example, recombinant fusion proteins comprising one of the above-mentioned proteins plus a multimerization domain, such as a leucine zipper, a coiled coil, an Fc portion of an immunoglobulin, or a substantially similar protein, can be produced using the methods of the invention. See e.g. WO94/10308; Lovejoy et al. (1993), Science 259:1288-1293; Harbury et al. (1993), Science 262:1401-05; Harbury et al. (1994), Nature 371:80-83; Håkansson et al. (1999), Structure 7:255-64. Specifically included among such recombinant fusion proteins are proteins in which a portion of a receptor is fused to an Fc portion of an antibody such as etanercept (a p75 TNFR:Fc), and belatacept (CTLA4:Fc). In another embodiment are antibody-drug conjugates.

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of". The section headings used herein are for organizational purposes only and are not to be construed as limiting the subject matter described. The methods and techniques described herein are generally performed according to conventional methods well known in the art and as described in various general and more specific references that are cited and discussed throughout the present specification unless otherwise indicated. Sec, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). All documents, or portions of documents, cited in this application, including but not limited to patents, patent applications, articles, books, and treatises, are hereby expressly incorporated by reference.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The following examples demonstrate embodiments and aspects of the disclosed methods and are not intended to be limiting.

EXAMPLES

Example 1

A small scale mock perfusion model was used to evaluate the effects of different carbon sources and their concentrations on high mannose glycoform modulation, cell growth, antibody production. A mock perfusion assay was performed in a 24 deep-well plate (Axygen, Union City, CA). Serum free, defined cell culture media were prepared containing 12 g/L mannose, galactose, fructose, maltose or glucose (sugars obtained from Sigma-Aldrich, St. Louis, MO) as the sole carbon source. The glucose containing media acted as the control. Briefly, each of the cell culture media were tested by using a CHO cell line expressing an IgG2 recombinant antibody (Cell line A) seeded at a targeted density ranging from 20 to $30 \times 10^6$ cells/mL in 3 mL of cell culture media per well. The cells were cultivated at 36° C., 5% $CO_2$, 85% relative humidity and shaken at 225 rpm in a 50-mm orbital diameter Kuhner incubator (Kuhner AG, Basel, Switzerland) for 3 or 4 days. Every 24 hours, cells were centrifuged at 200×g for 5 minutes (Beckman Coulter, Brea, CA) to collect the spent media and each well was then replenished with 3 mL fresh media. The collected spent media was analyzed for titer, viability, viable cell density and percent high mannose glycoform content (% HM). The cells were harvested on day 3 or 4 and cell counts and viability were measured. All experimental conditions were performed in duplicate.

Viable cell density and viability were determined using a Cedex cell counter (Roche Innovative, Beilefed, Germany). Metabolite information (glucose, lactate, ammonia, glutamine, glutamate) was obtained using NovaBioprofile Flex (Nova Biomedical, Waltham, MA). Antibody concentration in the spent media was determined using a Affinity Protein A Ultra Performance liquid chromatography (UPLC) (Waters Corporation, Milford, MA) equipped with a 50 mm×4.6 mm i.d. POROS A/20 protein A column (Life Technologies, Carlsbad, CA). After the sample was injected, the column was washed with Phosphate-Buffered Saline (PBS) pH=7.1 to remove CHO host cell proteins. Bound antibodies were then eluted in acidic PBS buffer (pH=1.9) and detected by UV absorbance at 280 nm to quantify antibody concentration. Packed cell volume was measured by spinning cells at 1462×g for 17 minutes. The adjusted titer was then calculated.

A high throughput microchip capillary electrophoresis method was used to determine the high mannose glycoform content on the recombinant antibodies using samples taken directly from the spent media. Samples were digested with endoglycosidase H (Endo H) for 2 hours at 37° C. After digestion, antibodies were denatured at 70° C. for 10 minutes and injected in to a LabChip GXII (Caliper Life Sciences, Hopkinton, MA) to quantify the amount of non-glycosylated heavy chain (NGHC). Samples not digested by Endo H were used as the controls. The % of NGHC from the control was subtracted by the % NGHC of test samples to yield the percent high mannose glycoform content (HM %) value.

Figure 1B:
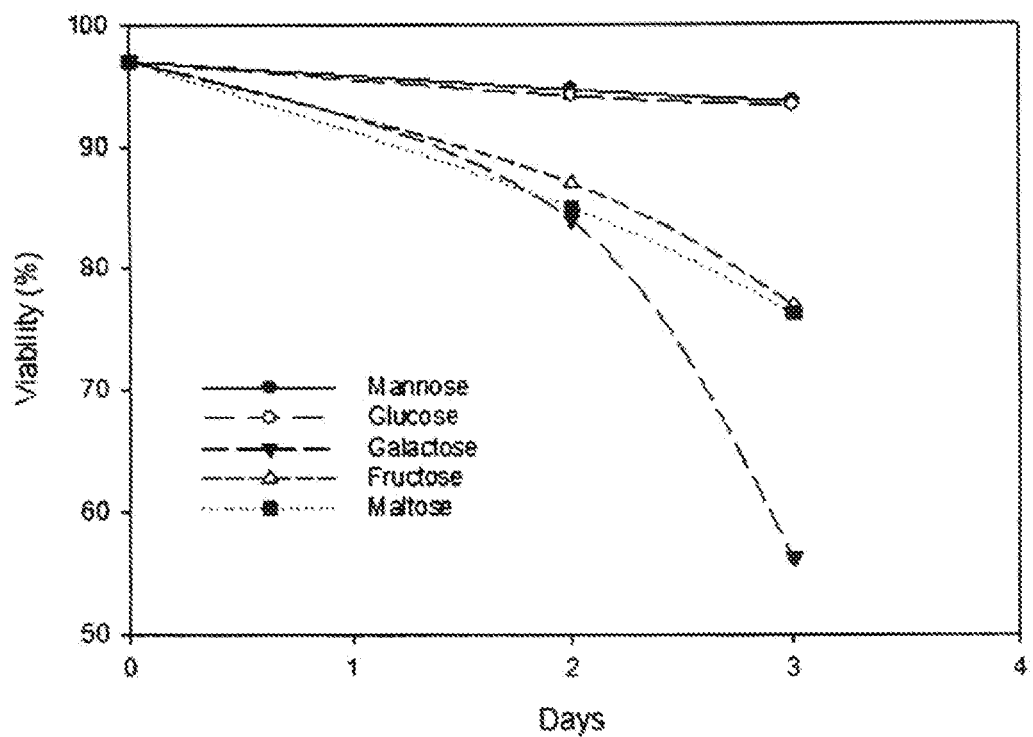
FIG. 1B shows a graph of effects of different carbon sources on viability.
Figure 1C:
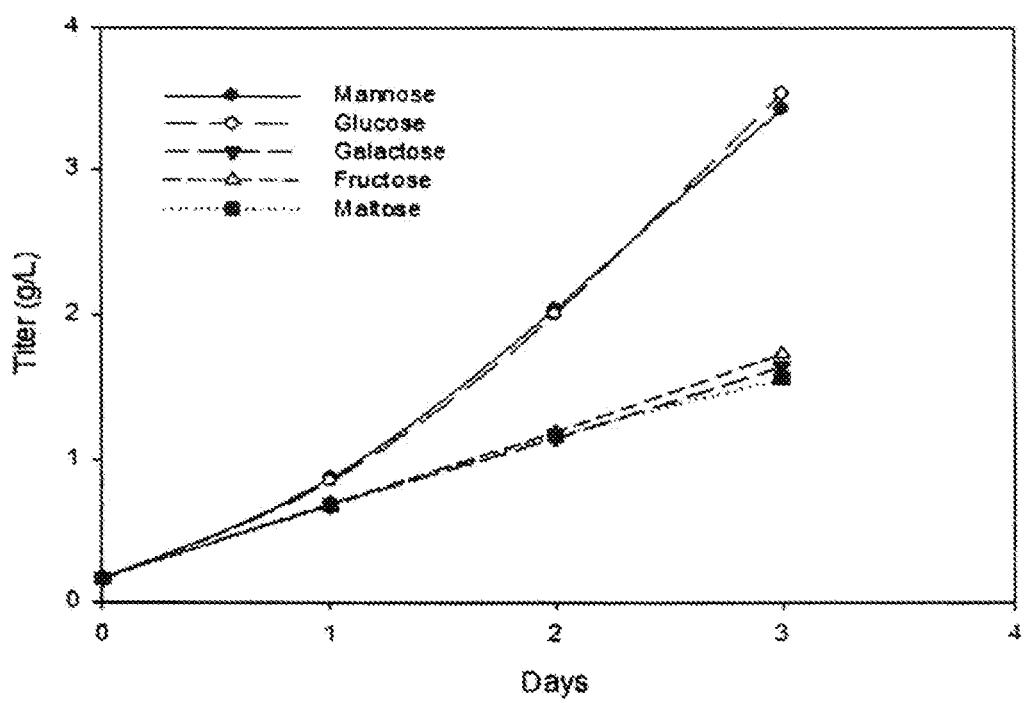
FIG. 1C shows a graph of effects of different carbon sources on antibody production.
Figure 1D:
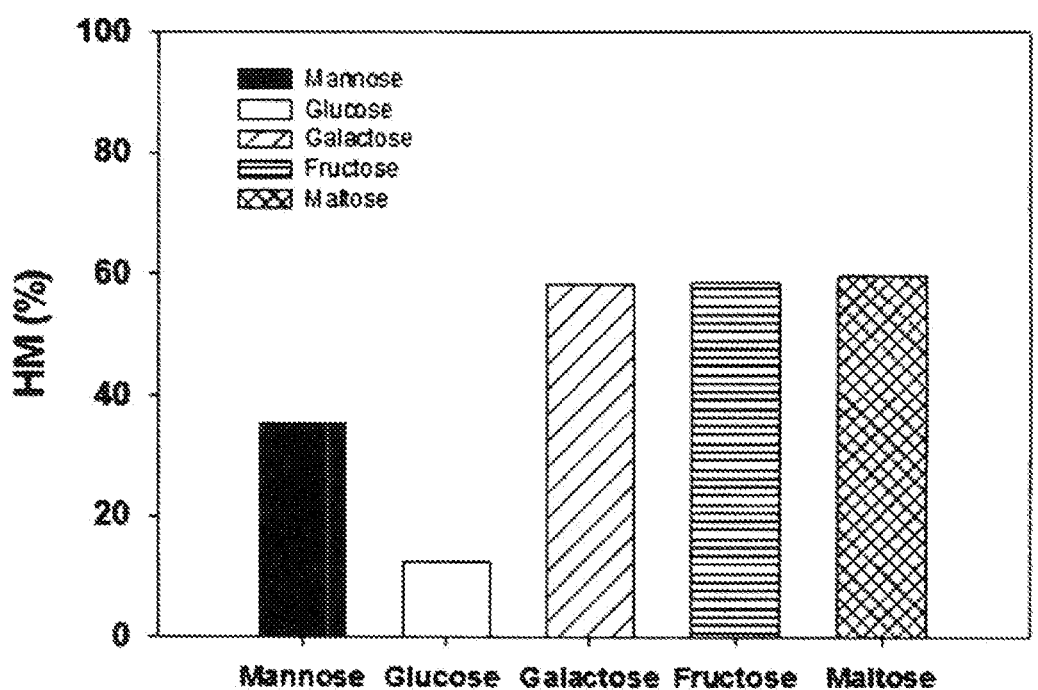
FIG. 1D shows a graph of effects of different carbon sources on % HM.

When galactose, fructose and maltose were metabolized, cell growth (viable cell density) was significantly inhibited as shown in FIG. 1A. Additionally, the viability and antibody titer were also negatively impacted (FIGS. 1B and 1C). After analysis of antibody quality attributes, it was found that the high mannose glycoform content was 59% in the galactose, fructose and maltose cultures, about five-fold higher than that of the glucose control (12%) (FIG. 1D). Interestingly, those cell cultures with mannose as the sole carbon source yielded growth, viability and antibody titer comparable with the glucose control (FIG. 1A to 1C). In the mannose cultures, viable cell density (VCD) continued to increase and reached $52 \times 10^6$ cells/mL with viability at 94% at day 3, and an antibody titer of 3.4 g/L. However, HM was 35% (FIG. 1D). This indicates that presence of mannose in the media affects glycan processing while maintaining growth and protein production levels equivalent to cell cultures grown in media supplemented with glucose only. Mannose in the cell culture media maintained cell growth and protein production equivalent to cultures grown in glucose media, while increasing upregulating high mannose glycoform content.

Based on the above results it was hypothesized that mannose concentration in the media could influence the high mannose glycoform content of the recombinant antibody being expressed. CHO cells may uptake mannose at a rate similar to glucose, so varying the ratio of mannose to glucose may yield different levels of high mannose glycoform content while having no negative impact on cell growth and antibody production. To test this hypothesis, serum free, defined cell culture media were prepared with glucose and mannose concentrations as shown in Table 1.

TABLE 1

Experimental design of using different glucose and mannose concentration in the media to study high mannose modulation effect.

| Media | Glucose (g/L) | Mannose (g/L) | Mannose/Total Hexose (M/H) ratio |
|---|---|---|---|
| G12M0 (control) | 12 | 0 | 0 |
| G9M3 | 9 | 3 | 0.25 |
| G6M6 | 6 | 6 | 0.5 |
| G3M9 | 3 | 9 | 0.75 |
| G0M12 | 0.75 | 11.25 | 0.94 |

Figure 2A:
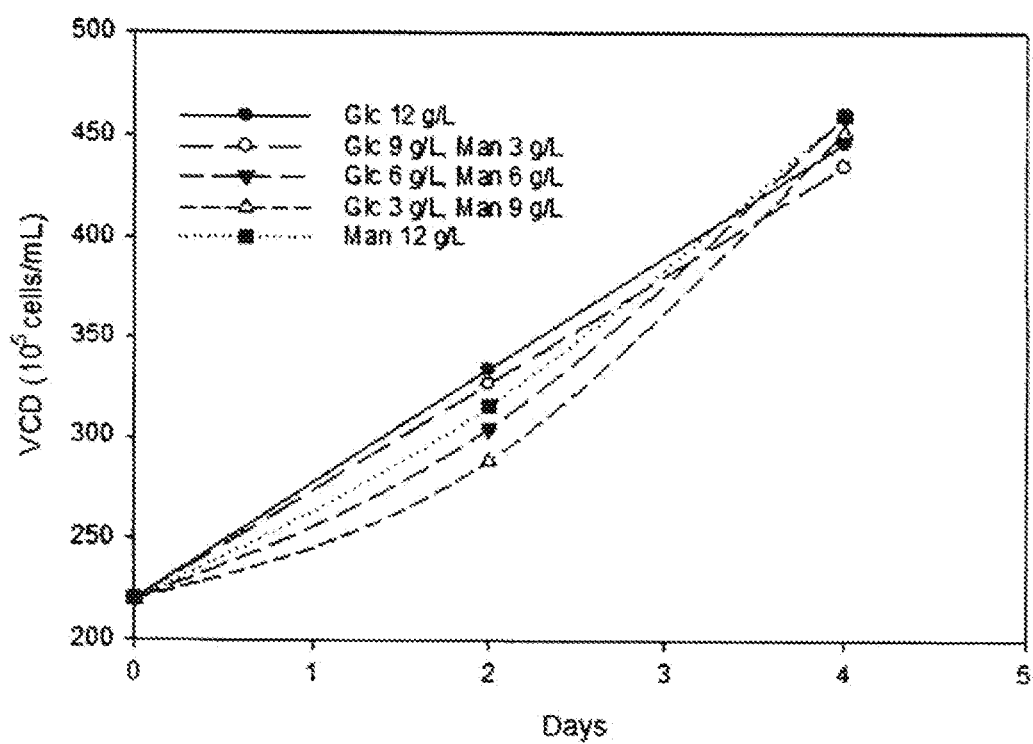
FIG. 2A shows a graph showing that titration of glucose by mannose in the media correlates with high mannose (HM) upregulation without impacting cell growth and antibody production. % HM.
Figure 2B:
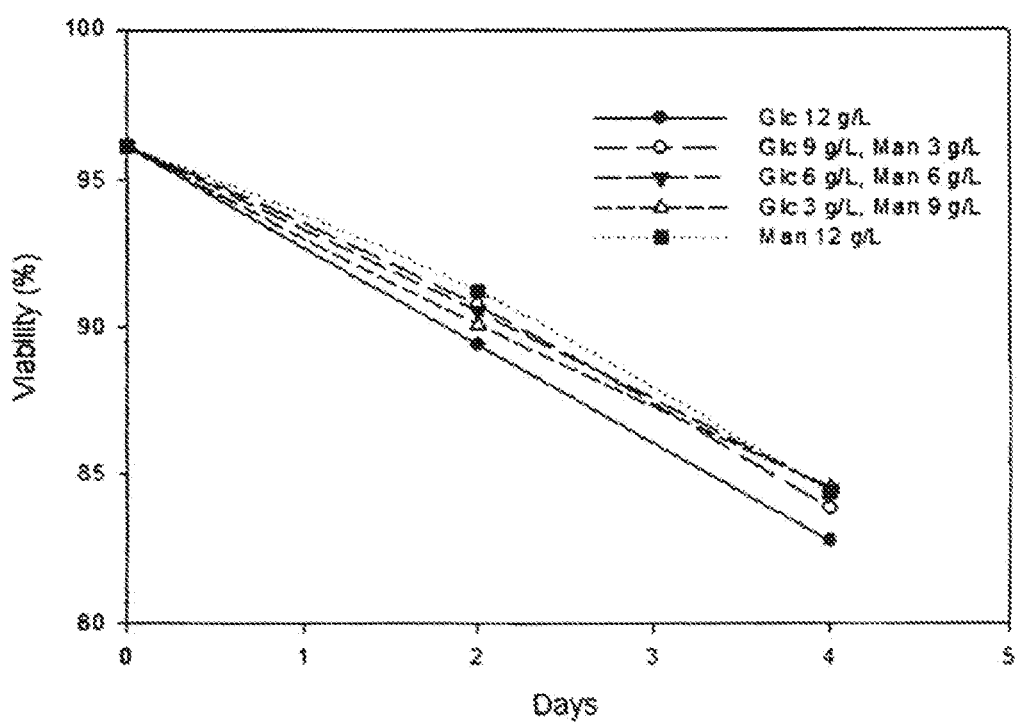
FIG. 2B shows a graph showing that titration of glucose by mannose in the media correlates with high mannose (HM) upregulation without impacting cell growth and antibody production. Viable cell density.
Figure 2C:
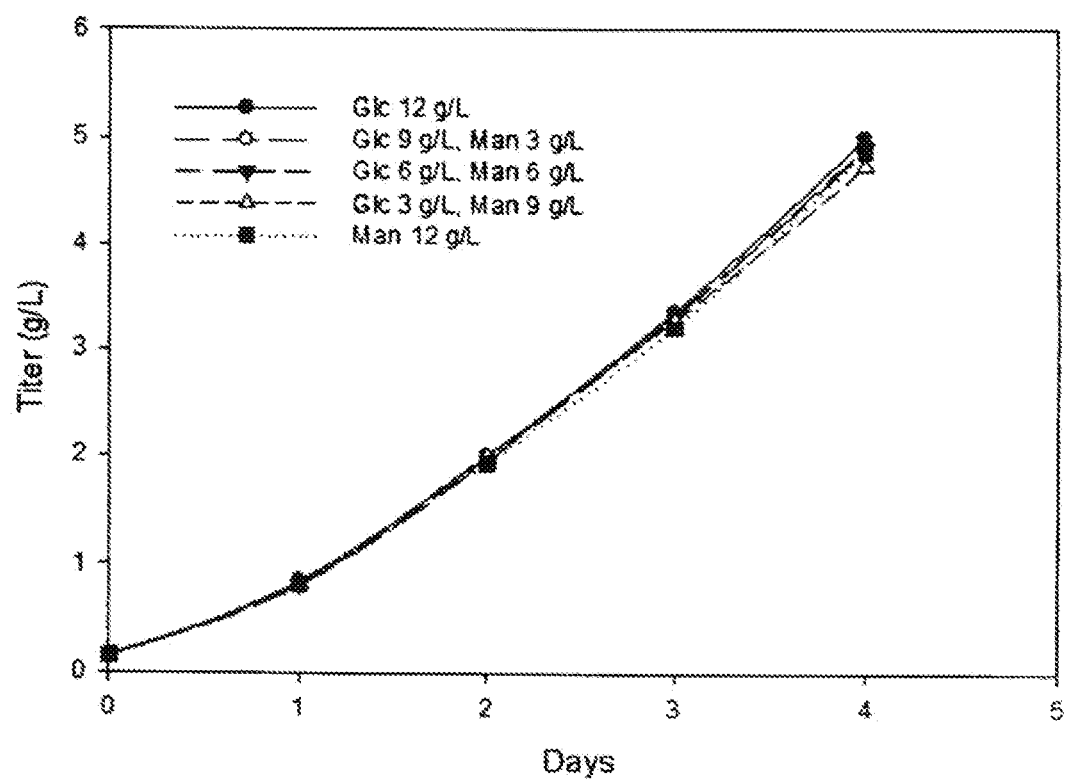
FIG. 2C shows a graph showing that titration of glucose by mannose in the media correlates with high mannose (HM) upregulation without impacting cell growth and antibody production. Viability.
Figure 2D:
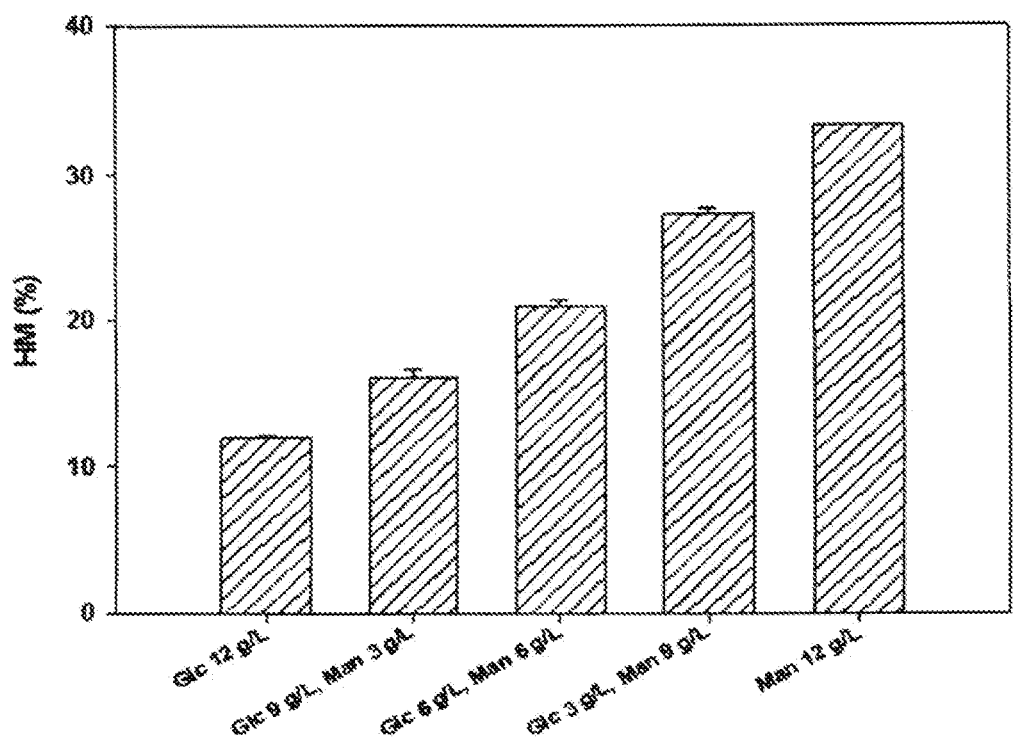
FIG. 2D shows a graph showing that titration of glucose by mannose in the media correlates with high mannose (HM) upregulation without impacting cell growth and antibody production. Antibody titer.

When the amount of glucose in the cell culture media was reduced and replaced with 3, 6, 9 and 11.25 g/L of mannose, the high mannose glycoform content increased from 12% to 16, 21, 27 and 33%, respectively (FIG. 2A). The viable cell density, viability and antibody titer were not affected compared to the 12 g/L glucose control (FIGS. 2 B, C and D). The results show that varying the ratio of mannose to glucose in the cell culture media could modulate the high mannose glycoform content (% HM) without alternating growth and productivity and that a linear correlation existed between percent high mannose glycoform content on the recombinant antibody and the mannose concentration provided in the cell culture media.

Figure 3A:
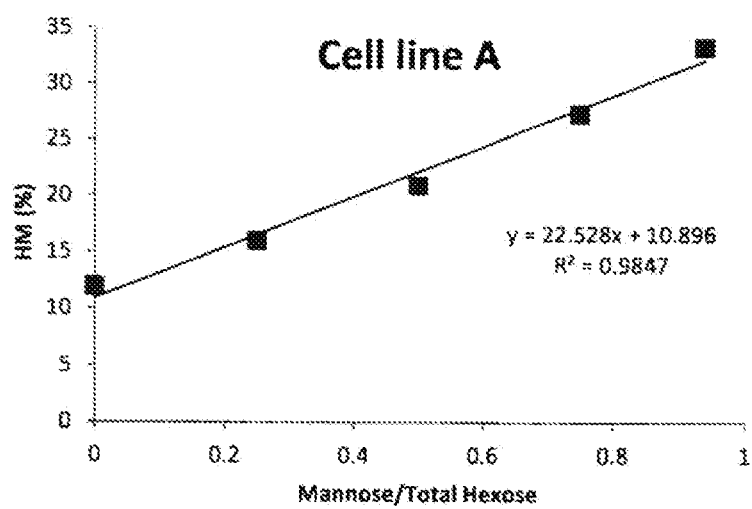
FIG. 3A shows a graph that demonstrates that high mannose (HM) modulation effect was universal and predictable across CHO cell lines expressing different antibodies (Cell line A).
Figure 3B:
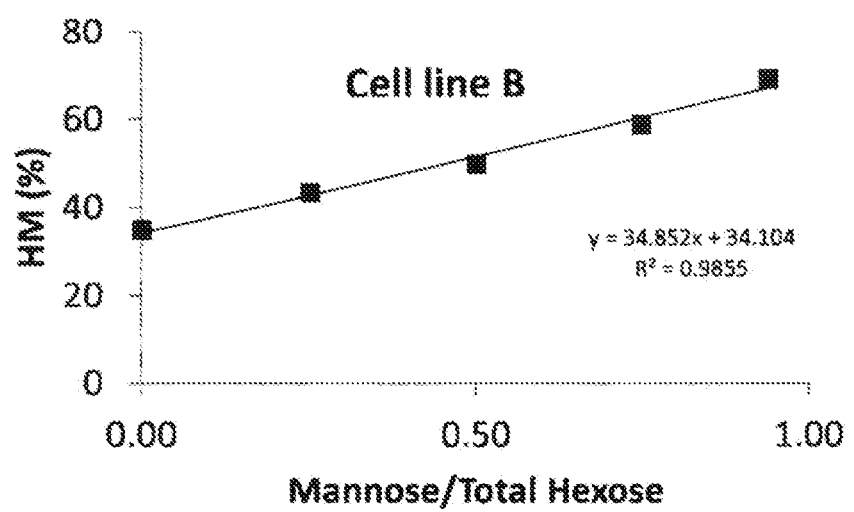
FIG. 3B shows a graph that demonstrates that high mannose (HM) modulation effect was universal and predictable across CHO cell lines expressing different antibodies. (Cell line B).
Figure 3C:
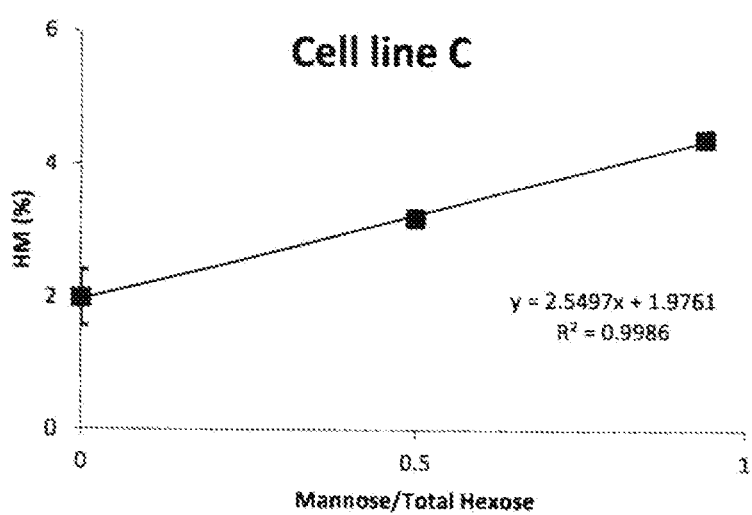
FIG. 3C shows a graph that demonstrates that high mannose (HM) modulation effect was universal and predictable across CHO cell lines expressing different antibodies (Cell line C).
Figure 3D:
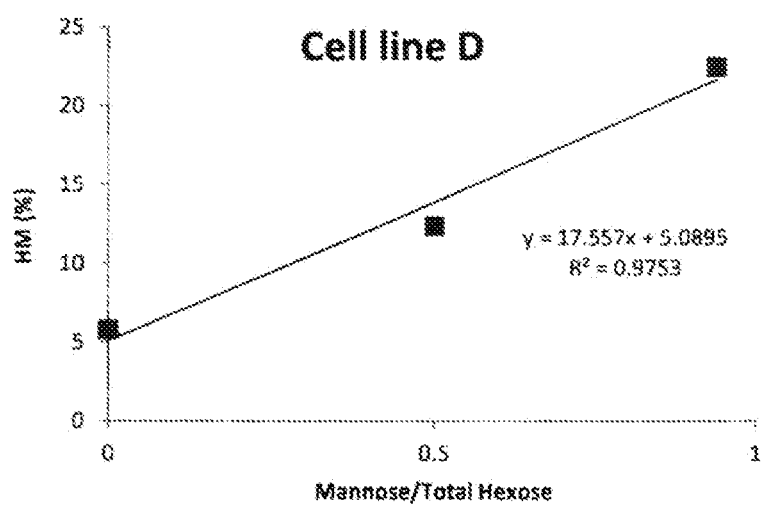
FIG. 3D shows a graph that demonstrates that high mannose (HM) modulation effect was universal and predictable across CHO cell lines expressing different antibodies (Cell line D).
Figure 3E:
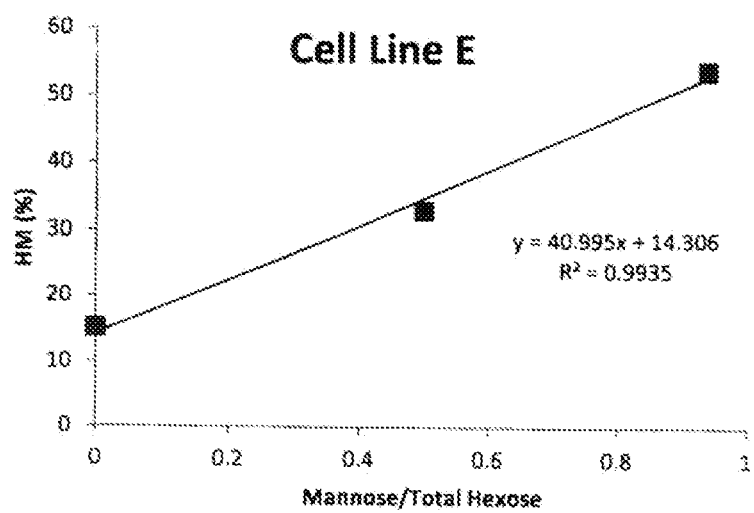
FIG. 3E shows a graph that demonstrates that high mannose (HM) modulation effect was universal and predictable across CHO cell lines expressing different antibodies (Cell line E).
Figure 4A:
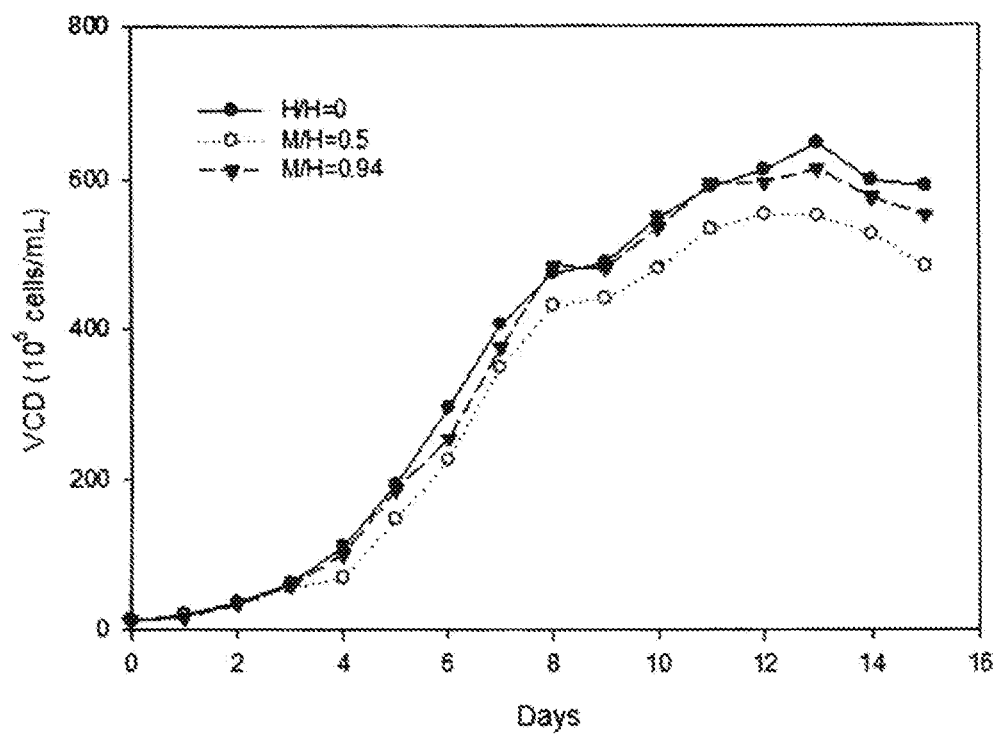
FIG. 4A shows a graph showing that high mannose (HM) modulation effect can be scaled up and maintain equivalent cell growth, viability and antibody titer using cell culture media having different mannose to total hexose (M/H) ratios. Viable cell density.
Figure 4B:
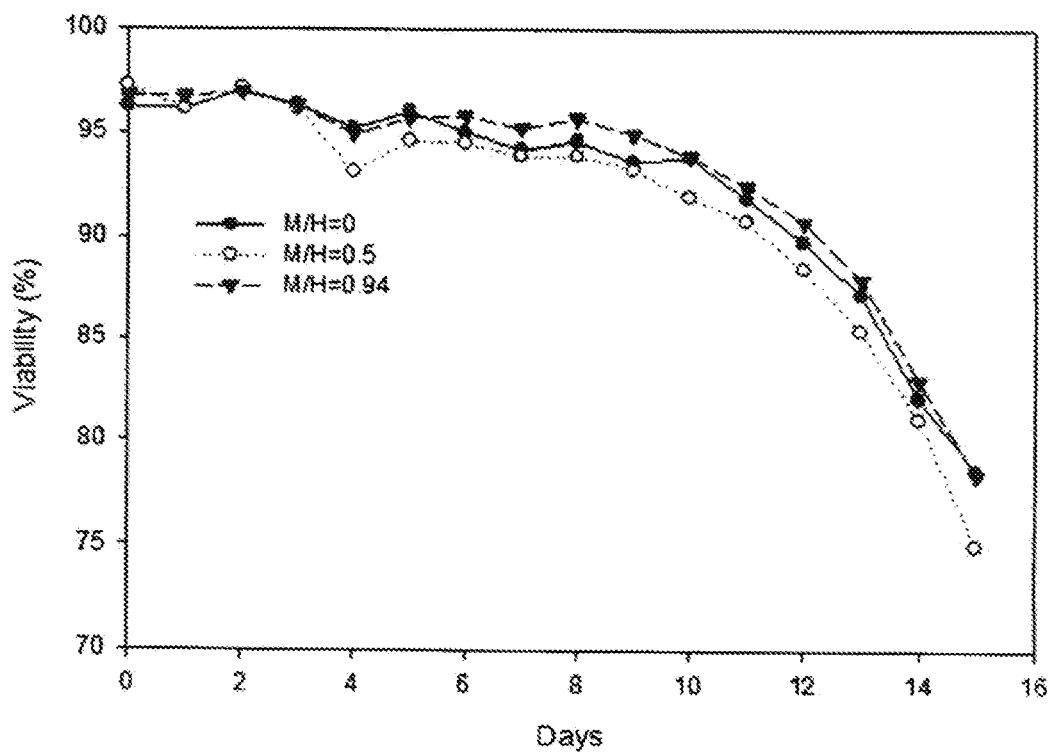
FIG. 4B shows a graph showing that high mannose (HM) modulation effect can be scaled up and maintain equivalent cell growth, viability and antibody titer using cell culture media having different mannose to total hexose (M/H) ratios. Viability.
Figure 4C:
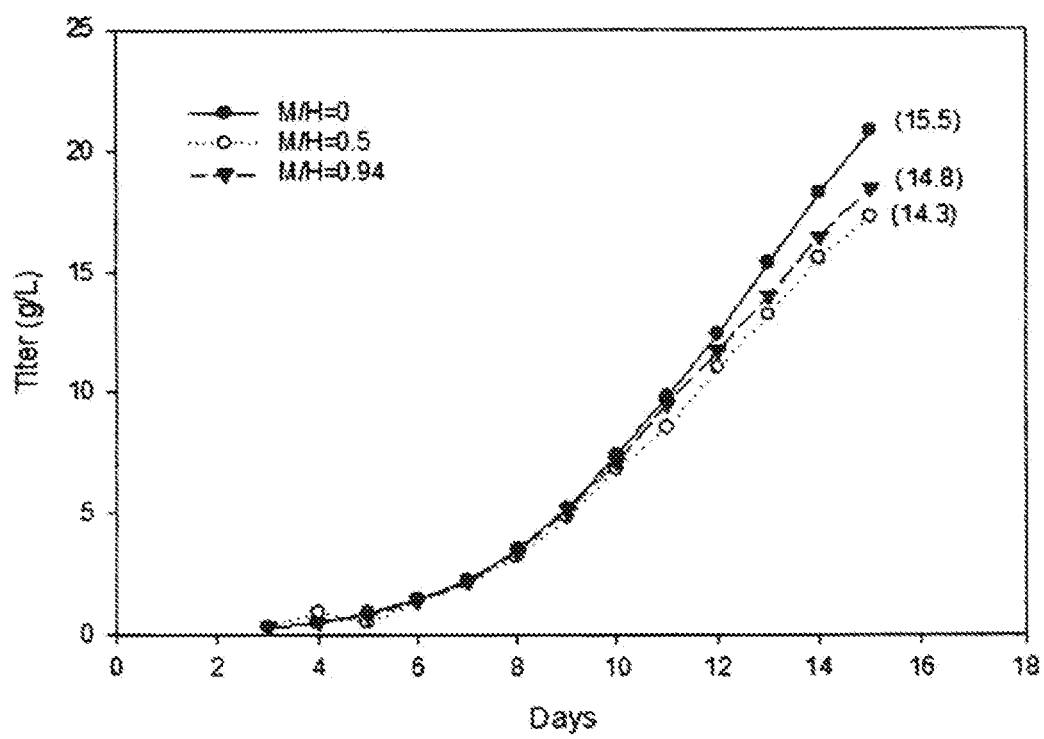
FIG. 4C shows a graph showing that high mannose (HM) modulation effect can be scaled up and maintain equivalent cell growth, viability and antibody titer using cell culture media having different mannose to total hexose (M/H) ratios. Antibody titer.
Figure 4D:
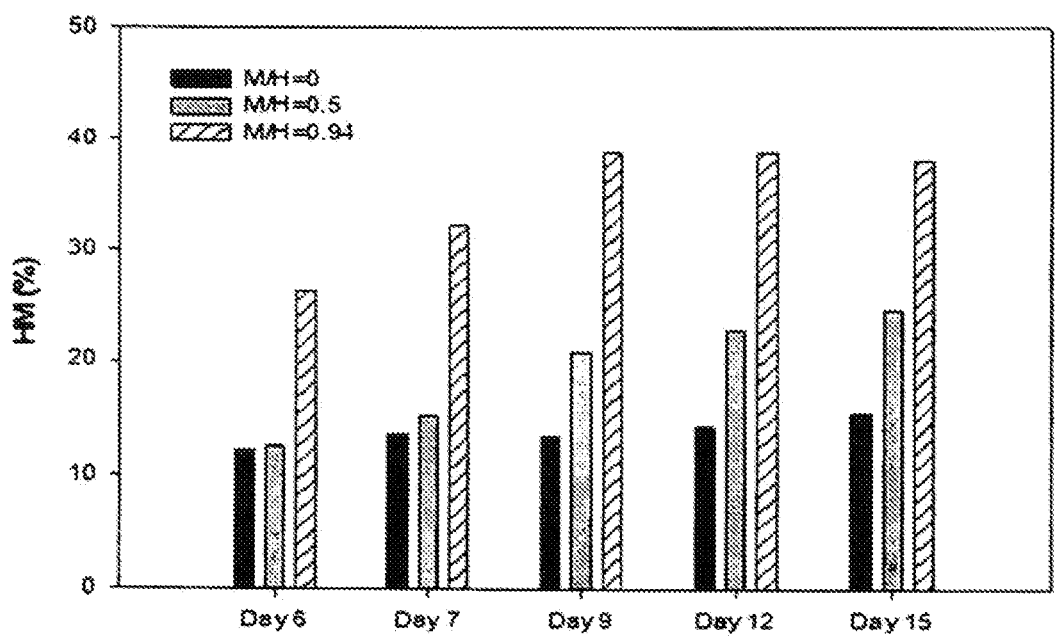
FIG. 4D shows a graph showing that high mannose (HM) modulation effect can be scaled up and maintain equivalent cell growth, viability and antibody titer using cell culture media having different mannose to total hexose (M/H) ratios. % HM.
Figure 5A:
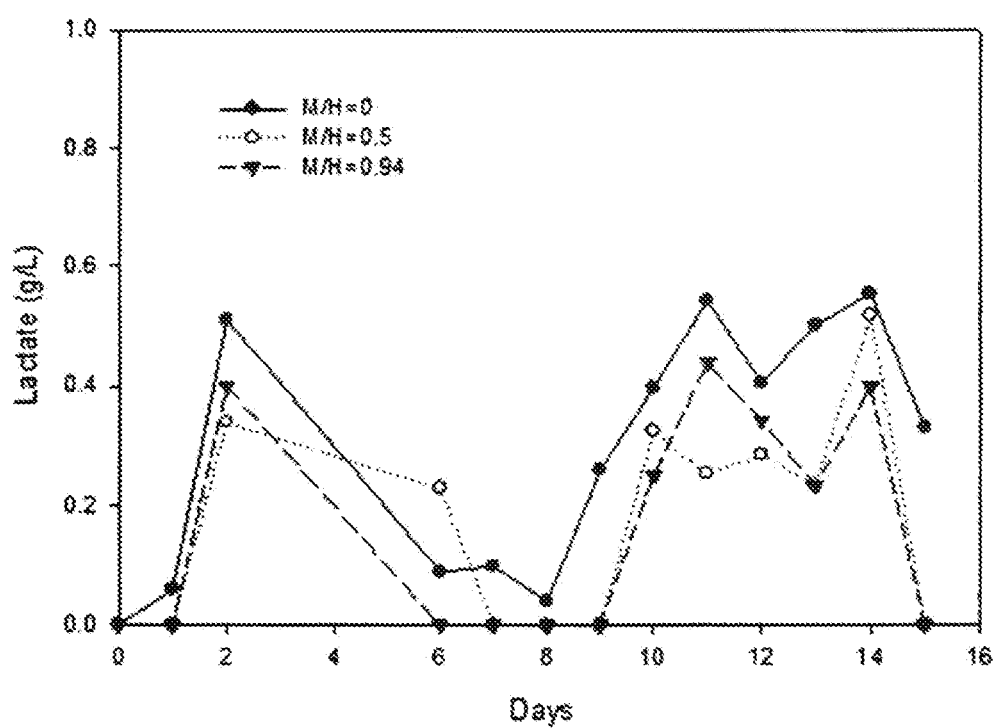
FIG. 5A shows a graph of metabolic profiles of three bioreactors with different mannose to total hexose ratios (M/H ratios) in the media. Glucose levels lower than 1 g/L may not be accurately measured by NovaFlex. Lactate
Figure 5B:
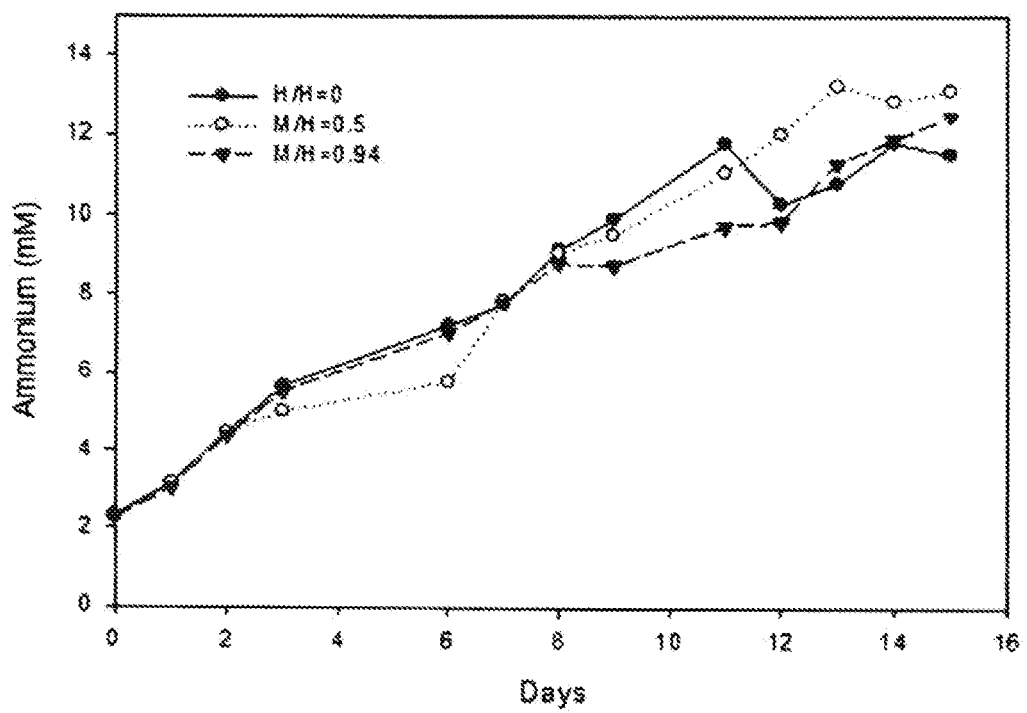
FIG. 5B shows a graph of metabolic profiles of three bioreactors with different mannose to total hexose ratios (M/H ratios) in the media. Glucose levels lower than 1 g/L may not be accurately measured by NovaFlex. Ammonia.
Figure 5C:
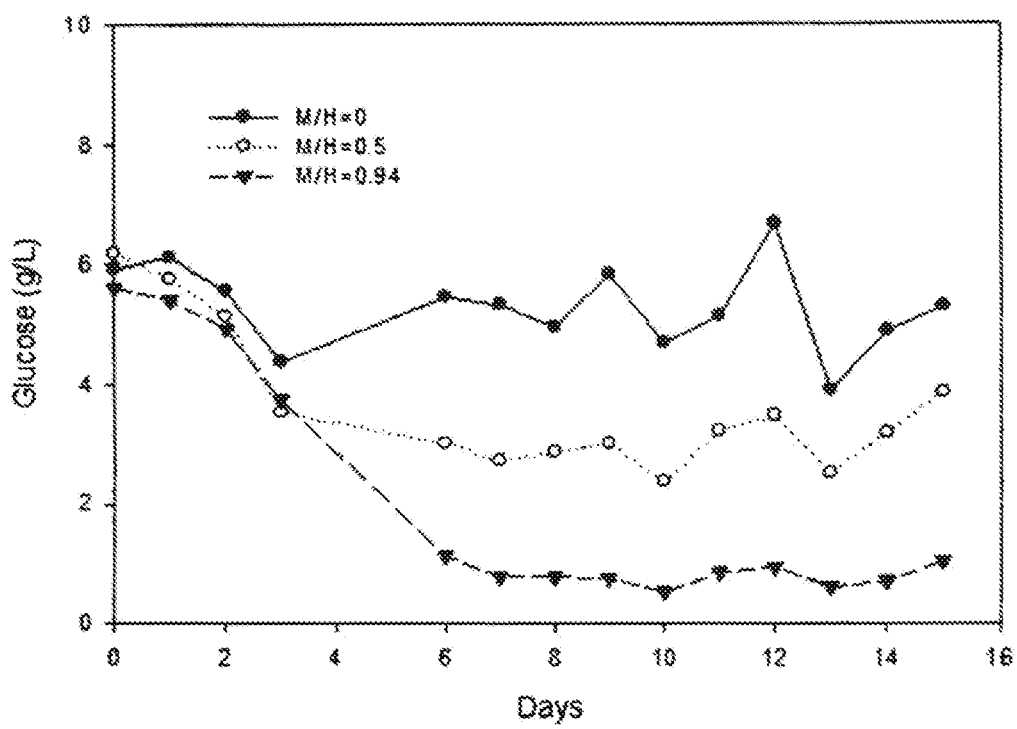
FIG. 5C shows a graph of metabolic profiles of three bioreactors with different mannose to total hexose ratios (M/H ratios) in the media. Glucose levels lower than 1 g/L may not be accurately measured by NovaFlex. Glucose.
Figure 5D:
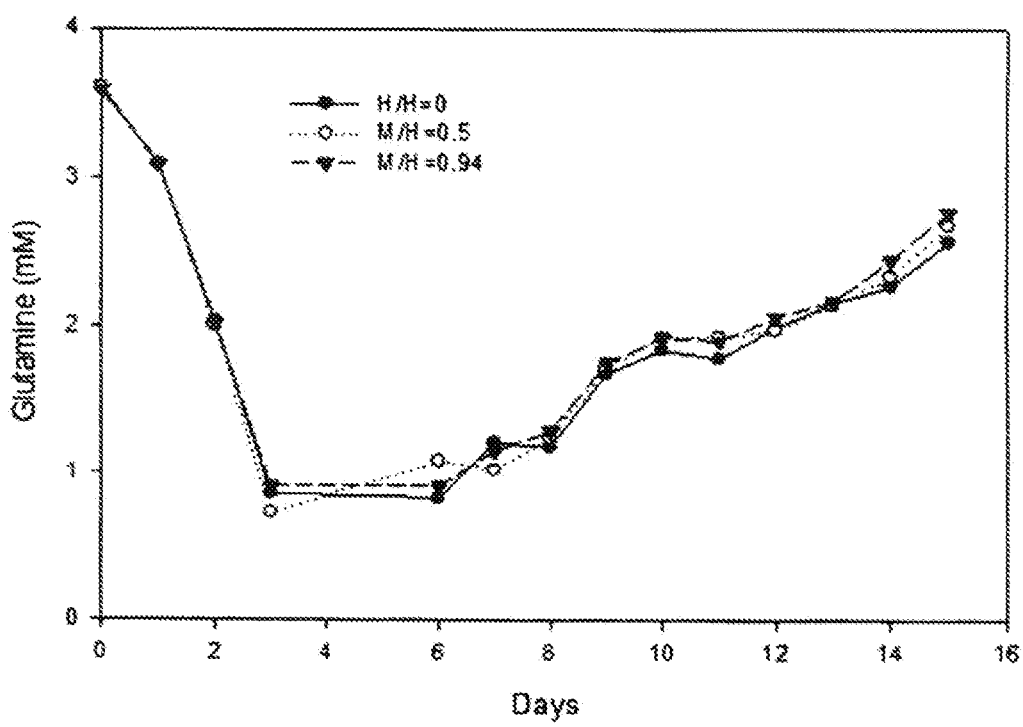
FIG. 5D shows a graph of metabolic profiles of three bioreactors with different mannose to total hexose ratios (M/H ratios) in the media. Glucose levels lower than 1 g/L may not be accurately measured by NovaFlex. Glutamine.

To test whether the modulation of the high mannose glycoform content was applicable across different antibody expressing cell lines, four other CHO cell lines (B, C, D and E) expressing IgG1 or IgG2 antibodies, were cultivated in the media containing the same mannose/glucose concentrations shown in Table 1. After harvest, samples were analyzed, and % HM value was plotted against the different mannose/total hexose (M/H) ratios of the media. As indicated in FIGS. 3A-3E, these four cell lines were all shown to have elevated % HM at high M/H ratio as see above for Cell line A. This result is striking especially considering that these cell lines have inherently different % HM for their respective antibodies. For example, cell line C produced an antibody with 2% HM in the control media with glucose only (M/H ratio 0.00) but the % HM increased to 4.4% at a M/H ratio of 0.94 (mannose at 11.25 g/L), FIG. 3C. On the other hand, Cell line B which would be considered a high % HM cell line, having a HM of 35% in the control media (M/H ratio 0.00), increased to 69% at the M/H ratio of 0.94 (FIG. 3B). A strong linear correlation between HM % and the M/H ratio was seen in all of the cell lines tested. This indicated that % HM of the produced antibodies could be controlled by specific M/H ratio in the cell culture media making the % HM of the produced antibodies predictable.

Example 2

To study the effect of different glucose/mannose ratios on HM % and to verify that the HM modulation effect is scalable, bioreactor runs using Cell line A were conducted. Three 3 L bench top bioreactors (Applikon Biotechnology, Forester City, CA) were equipped with ATF 2 systems (Refine Technology, Pine Brook, NJ) and 30 kDa cut-off hallow fiber cartridges (GE Healthcare Biosciences, Pittsburgh, PA) for media perfusion throughout the culture.

CHO Cell line A was seeded at $1.4 \times 10^6$ cells/mL in the bioreactors containing 1.5 L of serum free, defined growth media containing 6.25 g/L glucose as the only carbon source. An automated bioprocessing software was used for data acquisition and parameter control. Starting on day 3, the bioreactors were perfused with serum free, defined cell culture media containing different concentrations of glucose and mannose as the only carbon sources, see Table 2.

TABLE 2

Glucose and mannose concentration in perfusion cell culture media

| Glucose (g/L) | Mannose (g/L) | Mannose/Total Hexose (M/H) ratio |
|---|---|---|
| 12 (control) | 0 | 0 |
| 6 | 6 | 0.5 |
| 0.75 | 11.25 | 0.94 |

During the culture process the cells were initially grown at 36° C. with agitation of 150 rpm and an air flow rate of 100 cm$^3$/min, and shifted to 33° C. once the cell density reached 35 to $40 \times 10^6$ cells/mL. The dissolved oxygen level was maintained at 60% of air saturation and supplemented with pure oxygen when needed. The pH of the culture media was maintained at 7.0 by media $CO_2$ level or 1M sodium carbonate.

The permeate was collected at the same rate as the perfusion rate. The perfusion rate increased gradually from 0.5 to 1.0 working volume/day over the 15 day run. During the cultivation period, samples were taken daily, and cell counts, cell viability and metabolites were measured. Viable cell density, viability, titer and other measurements were made as described above. Antibodies from bioreactor samples were first purified by affinity protein A MediaScout MiniChrom column (ATOLL, Weingarten, Germany) before the high mannose assay. The purified protein was digested with Endo H and denatured as described above. The percentage of NGHC from the digested samples and the controls were determined using ProteomeLab PA800 Capillary Electrophoresis system (Beckman Coulter, Brea, CA), and two NGHC values were used to determine the HM % of the recombinant antibody.

FIGS. 4A-D show the time course for viable cell density, viability, antibody titer and % HM from the three tested bioreactors. For the cell culture perfused with the media having an M/H ratio of 0.94, the VCD reached $55 \times 10^6$ cells/mL with 78% viability and the adjusted titer of 14.3 g/L, which were were all equivalent to the control. The metabolic profiles are shown in FIGS. 5A-5D.

Cell growth, viability and titer were all slightly lower for M/H ratio of 0.5. This is likely due to an operational deviation for this condition. A base dump deviation at day 3 in the reactor with M/H ratio of 0.5 showed elevated osmolarity for 12 hours. The high osmolarity might contribute to the slightly low VCD, viability and antibody titer compared to other two conditions FIGS. 4A-4C.

As shown in the Table 3, certain glycans, including M3G0F, A2G1F, A2G2F, sialylated and aglycosylated forms, were not affected by different M/H ratios in the media.

TABLE 3

Glycan maps from bioreactor samples with various M/H ratios

| M/H ratio | HM (%) | M3G0F (%) | A2G0F (%) | A2G1F (%) | A2G2F (%) | Afucosylated complex (%) | Sialyated (%) | Unknown glucan (%) | Aglycosylated (%) |
|---|---|---|---|---|---|---|---|---|---|
| 0 | 13.4 | 5.9 | 63.1 | 9.0 | 0.8 | 3.8 | 0.6 | 2.2 | 2.2 |
| 0.5 | 19.8 | 5.5 | 50.5 | 11.9 | 1.3 | 4.8 | 0.8 | 3.4 | 1.6 |
| 0.94 | 30.6 | 5.9 | 40.4 | 8.9 | 0.8 | 5.6 | 0.7 | 5.0 | 2.9 |

For HM content, the three test conditions showed different dynamic profiles. The control had HM of 12% at day 6 and increased gradually to 15% at day 15. When M/H ratio was 0.5, the HM was also 12% at day 6, but increased two-fold to 24% at day 15. Interestingly, the culture grown in the media having an M/H ratio of 0.94 was initially produced at a high HM of 26% and reached 38% at day 9 and plateaued. This indicates HM upregulation by mannose may exhibit a cap limitation effect.

Figure 6:
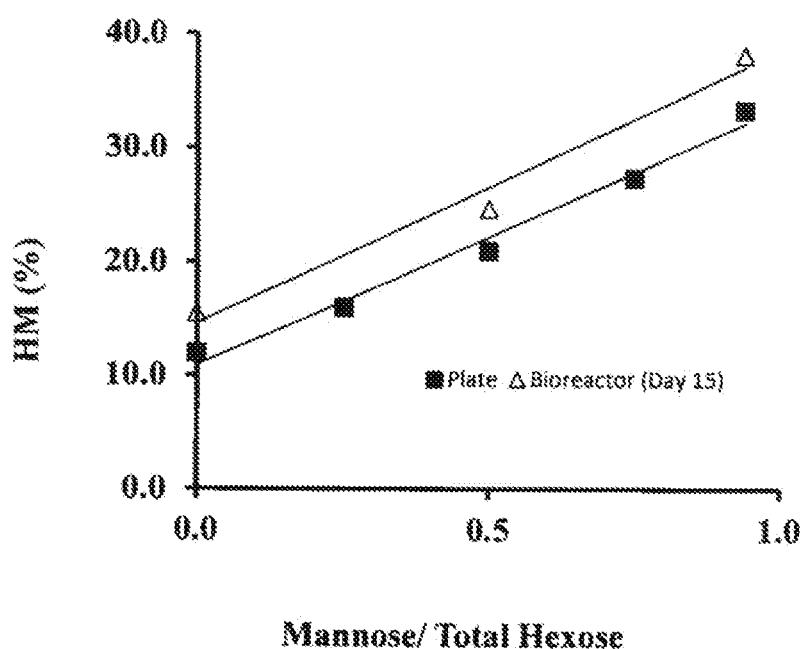
FIG. 6 shows a good correlation was demonstrated between mock perfusion samples and bioreactor samples regarding the high mannose (HM) modulation effect and its predictability with different mannose to total hexose ratios (M/H ratio). Square: mock perfusion; Circle: bioreactor.

These results indicate that the HM modulation effect is applicable at larger scale. This effect is also predictable with an R-squared value of 0.98 (FIG. 6). A good correlation was seen between the mock perfusion and bioreactor results. FIG. 6 compares the HM modulation effect between Cell line A in the mock perfusion and at Day 15 of the bioreactor run. The slops of the trend lines are 22.5 and 23.8 for mock perfusion and bioreactor, respectively, demonstrating the correlation was scale independent.

Traditionally, when cells are cultured in flasks or on plates, physical parameters and nutritional components are not well-controlled. Hence, scale variations regarding cell growth, protein production and glycosylation pattern are commonly observed in cell culture processes (Altamirano, et al. (2000) Biotechnol Prog 16, 69-75). In these experiments, it was surprising that there was a good correlation between the mock perfusion assay and bioreactor scale cell cultures regarding the HM modulation effects. This discovery makes the method even more attractive as the bioreactor % HM becomes predictive. The high cell density inoculation and daily media exchange which maintains a good pH control in the mock perfusion might contribute to this correlation.

Example 3

To understand the overall glycan effect by mannose modulation, antibodies produced by Cell line A from the process described in Example 2 were analyzed with a full glycan map assay using hydrophilic-interaction liquid chromatography (HILIC). The purified antibodies were digested by N-glycosidase F (New England BioLabs, Ipswich, MA) at 37° C. for 2 hours to release the glycans. The released glycans were labeled with 2-aminobenzoic acid and purified using GlycoClean S cartridges (Prozyme, Heyward, CA) according to the manufacturer's directions. The purified glycans were then desalted and reconstituted in water for use in the assay. HILIC chromatography was performed with a 100 mm×2.1 mm i.d BEH Glycan column using UPLC (Waters Corporation, Milford, MA) and the eluted glycans were detected, identified, and qualified by a fluorescence detector based on different elution times of different glycans.

A high M/H ratio increased the % HM and decreased the percent of A2G0F. The M/H ratio of 0.94 had the highest HM level of 30.6% and the lowest A2G0F level of 40.4%. In addition, an increased M/H ratio produced a higher amount of afucosylated complex. A few existing unidentified glycan forms also increased to a small extent. The percentage of each HM species was also identified and compared (Table 4).

TABLE 4

Percentages of various HM species from bioreactor samples with various M/H ratios

| M/H ratio | High Mannose (%) | Man8 (%) | Man7 (%) | Man6 (%) | Man5 (%) |
|---|---|---|---|---|---|
| 0 | 13.4 | 0.4 | 0.4 | 0.6 | 12 |
| 0.5 | 19.8 | 1.2 | 1.8 | 2.4 | 14.4 |
| 0.94 | 30.6 | 2.5 | 3.1 | 5.9 | 19.2 |

It is known that GDP-mannose converts to GDP-fucose by GDP-mannose 4,6-dehydratase (GMD). GDP-fucose is also a potent inhibitor of GMD (Becker and Lowe, (2003) Glycobiology 13, 41R-53R). It is speculated that high mannose concentration increases the influx of GDP-mannose, therefore, high intracellular GDP-fucose and fucosylation were expected. The increased afucosylated complex may be due to a strong feedback inhibition of GDP-fucose to GMD or by unidentified mechanisms. The galactosylation and sialylation remain similar upon the addition of mannose in the culture media. The decrease of A2G0F correlates with HM increase. These results illustrate that only the early glycosylation pathway (before A2G0F) is majorly affected.

With an increase in M/H ratio, the levels of Man8, Man7, Man6 and Man5 glycans were all significantly increased when compared to the control. Man5 was found to be the major HM species in all the three conditions; however Man6 to Man8 appeared to increase significantly at higher M/H ratios (Table 4). Considering antibody glycan processing, these results suggest that high M/H ratio slows down early glycan processing steps, leading to the elevated level of all HM species. With an increase of H/M ratio, more primitive high mannose species were found in the produced antibodies.

Figure 7:
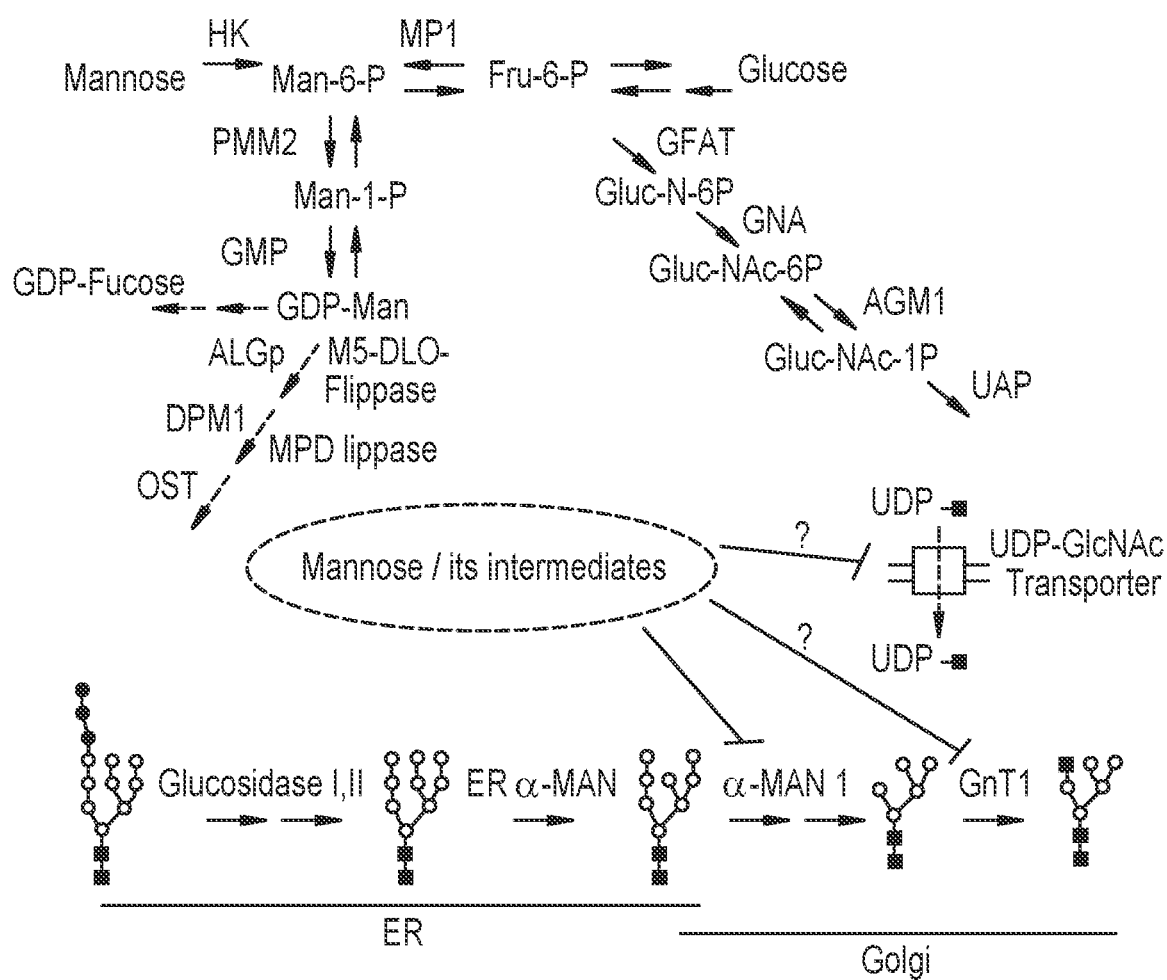
FIG. 7 shows possible mechanisms contributing to the high mannose upregulation in high mannose to total hexose ratio media. Three pathways, including GDP-mannose biosynthesis, early glycosylation and GluNAc biosynthesis, may involve in increased accumulation of different high mannose species.

The HM species accumulation profile further suggests that two glycosylation steps, HM trimming by α-mannosidase I (α-MAN I) and GluNAc addition by GluNAc transferase (GnT1), are inhibited, increasing the HM % (FIG. 7). The first step for a cell to utilize intracellular mannose is to convert mannose to mannose-6-phosphate, a key metabolite bridging energy generation (glycolysis) and N-glycan biosynthesis (Alton et al., (1998) Glycobiology 8, 285-95).

Elevated intracellular M6P level has been demonstrated in mouse embryonic fibroblasts when 10 mM of mannose was supplemented in the media (Gao et al., (2011) Mol Biol Cell 22, 2994-3009). Therefore, it is reasonable to theorize that elevated M6P level should also be found in high M/H ratio culture, suggesting a possible flux increase for N-glycan biosynthesis. As illustrated in FIG. 7, three pathways, GDP-mannose biosynthesis, early glycosylation and GluNAc biosynthesis, may involve in HM upregulation in this study. Increased levels of primitive HM species suggest that presence of mannose of its intermediates (M6P, MIP or GDP-Mannose) may directly or indirectly inhibit α-mannosidase I activity. High Man5 levels also suggest GluNAc pathway might also be involved. However, our data shows that the elevated Man5 level is not related to GDP-GluNAc limitation due to glucose limitation effect (Table 5). Instead, it is more likely that mannose or its intermediates affect GDP-GluNAc transportation or GnT1 activity.

TABLE 5

% HM, residual glucose concentration in the media for Cell line A

| Media | High Mannose (%) | Residual Glucose (g/L) |
|---|---|---|
| G12M0 | 12.0 | 4.15 |
| G9M3 | 16.0 | 2.86 |
| G6M6 | 21.0 | 1.35 |
| G3M9 | 27.3 | 0.97 |
| G0M12 | 33.3 | 0.16 |

What is claimed is:

1. A method for controlling Mannose-5 glycoform content of Immunoglobulin 2 (IgG2) molecules, wherein said glycoform content is measured as percentage of Mannose-5 glycoforms, and wherein the percentage of Mannose-5 glycoforms in the IgG2 molecules is increased as compared to a control value, comprising:
   (a) establishing a CHO cell culture in a bioreactor with CHO cells that express IgG2 and with a first cell culture medium that does not comprise mannose;
   (b) growing the CHO cells in said first culture medium until viable cell density is at least $3 \times 10^6$ cells/mL;
   (c) providing the CHO cell culture with a second culture medium, wherein said second culture medium comprises mannose and glucose, and wherein the ratio of mannose concentration to total hexose concentration in the second medium is between 0.1 and 0.4; and
   (d) recovering the IgG2 molecules from the cell culture.

2. The method of claim 1, further comprising purifying the IgG2 molecules.

3. The method of claim 2, wherein the purified IgG2 molecules are formulated into a pharmaceutically acceptable formulation.

4. The method of claim 1, wherein the ratio of mannose concentration to total hexose concentration in the second medium is between 0.2 and 0.4.

5. The method of claim 1, wherein in step (c), the second culture medium is provided by one or more bolus feeds.

6. The method of claim 5, wherein said one or more bolus feeds each comprises mannose and glucose, and wherein the ratio of mannose concentration to total hexose concentration in the bolus feed is between 0.1 and 0.4.

7. The method of claim 1, wherein in step (c), the second culture medium is provided by perfusion.

8. The method of claim 7, wherein said perfusion medium comprises mannose and glucose, and wherein the ratio of mannose concentration to total hexose concentration in the perfusion medium is between 0.1 and 0.4.

9. The method of claim 1, wherein the viable cell density reaches at least $10 \times 10^6$ cells/mL before the cells are fed with the second culture medium.

10. The method of claim 1, wherein the viable cell density reaches at least $20 \times 10^6$ cells/mL before the cells are fed with the second culture medium.

11. The method of claim 1, wherein the viable cell density is between $10 \times 10^6$ cells/mL and $60 \times 10^6$ cells/mL when the cells are fed with the second culture medium.

12. The method of claim 1, wherein the viable cell density is between $10 \times 10^6$ cells/mL and $40 \times 10^6$ cells/mL when the cells are fed with the second culture medium.

13. The method of claim 1, wherein the viable cell density reaches at least $25 \times 10^6$ cells/mL before the cells are fed with the second culture medium.

14. A method for controlling Mannose-5 glycoform content of IgG2 molecules, wherein said glycoform content is measured as percentage of Mannose-5 glycoforms, and wherein the percentage of Mannose-5 glycoforms in the IgG2 molecules is increased as compared to a control value, comprising:
   (a) establishing a CHO cell culture in a bioreactor by inoculating at least $0.5 \times 10^6$ cells/mL CHO cells in a first cell culture medium on day 0, wherein said first cell culture medium is serum-free and does not comprise mannose, and wherein said CHO cells express said IgG2;
   (b) switching the CHO cell culture to a second culture medium at a time that is between day 3 to day 9, wherein said second culture medium comprises mannose and glucose, and wherein the ratio of mannose concentration to total hexose concentration in the second medium is between 0.1 and 0.4; and
   (c) recovering the IgG2 molecules from the cell culture.

15. The method of claim 14, further comprising purifying the IgG2 molecules.

16. The method of claim 15, wherein the purified IgG2 molecules are formulated into a pharmaceutically acceptable formulation.

17. The method of claim 14, wherein the ratio of mannose concentration to total hexose concentration in the second medium is between 0.2 to 0.4.

18. The method of claim 14, wherein in step (b), the second culture medium is provided by one or more bolus feeds.

19. The method of claim 18, wherein said one or more bolus feeds each comprises mannose and glucose, and wherein the ratio of mannose concentration to total hexose concentration in the bolus feed is between 0.1 and 0.4.

20. The method of claim 14, wherein in step (b), the second culture medium is provided by perfusion.

21. The method of claim 20, wherein said perfusion medium comprises mannose and glucose, and wherein the ratio of mannose concentration to total hexose concentration in the perfusion medium is between 0.1 and 0.4.

22. A method for controlling Mannose-5 glycoform content of IgG2 molecules, wherein said glycoform content is measured as percentage of Mannose-5 glycoforms, and wherein the percentage of Mannose-5 glycoforms in the IgG2 molecules is increased as compared to a control value, comprising:
   (a) establishing a CHO cell culture in a bioreactor with CHO cells that express the IgG2, and with a first cell culture medium that comprises glucose;

(b) growing the CHO cells in said first culture medium until viable cell density is at least $3\times10^6$ cells/mL;

(c) providing the CHO cell culture with a second culture medium, wherein said second culture medium comprises mannose and glucose, and wherein the ratio of mannose concentration to total hexose concentration in the second medium is between 0.1 and 0.4; and (d) recovering the IgG2 molecules from the cell culture.

23. The method of claim 22, wherein the viable cell density is between $10\times10^6$ cells/mL and $60\times10^6$ cells/mL when the cells are fed with the second culture medium.

24. The method of claim 22, wherein the ratio of mannose concentration to total hexose concentration in the second medium is between 0.2 to 0.4.

25. The method of claim 22, wherein in step (c), the second culture medium is provided by one or more bolus feeds.

26. The method of claim 22, wherein in step (c), the second culture medium is provided by perfusion.

27. The method of claim 22, wherein in step (a), said first culture medium does not comprise mannose.

28. The method of claim 22, further comprising purifying the IgG2 molecules.

29. The method of claim 28, wherein the purified IgG2 molecules are formulated into a pharmaceutically acceptable formulation.

* * * * *